US 12,364,800 B2

United States Patent
Maruya et al.

(10) Patent No.: US 12,364,800 B2
(45) Date of Patent: Jul. 22, 2025

(54) MONITORING APPARATUS AND ASSISTED CIRCULATION APPARATUS

(71) Applicant: SENKO MEDICAL INSTRUMENT Mfg. Co., Ltd., Tokyo (JP)

(72) Inventors: Taku Maruya, Tokyo (JP); Shoichi Tsukakoshi, Tokyo (JP); Shinji Goto, Tokyo (JP)

(73) Assignee: SENKO MEDICAL INSTRUMENT Mfg. Co., Ltd., Tokyo (JP)

( * ) Notice: Subject to any disclaimer, the term of this patent is extended or adjusted under 35 U.S.C. 154(b) by 0 days.

(21) Appl. No.: 18/039,681

(22) PCT Filed: Dec. 2, 2021

(86) PCT No.: PCT/JP2021/044342
§ 371 (c)(1),
(2) Date: Dec. 5, 2023

(87) PCT Pub. No.: WO2022/118931
PCT Pub. Date: Jun. 9, 2022

(65) Prior Publication Data
US 2024/0238497 A1    Jul. 18, 2024

(30) Foreign Application Priority Data
Dec. 2, 2020    (JP) .................. 2020-200580

(51) Int. Cl.
*A61M 1/36*    (2006.01)
*G16H 50/30*   (2018.01)

(52) U.S. Cl.
CPC ........ *A61M 1/3666* (2013.01); *A61M 1/3603* (2014.02); *G16H 50/30* (2018.01);
(Continued)

(58) Field of Classification Search
CPC .............. A61M 1/1611; A61M 1/3603; A61M 1/3607; A61M 1/3609; A61M 1/3666;
(Continued)

(56) References Cited

U.S. PATENT DOCUMENTS

2017/0095601 A1*   4/2017   Laubscher .......... A61M 1/1601

FOREIGN PATENT DOCUMENTS

| CN | 104379054 A | 2/2015 |
| CN | 107592818 A | 1/2018 |

(Continued)

OTHER PUBLICATIONS

Office Action, with translation of Search Report, received in corresponding CN Application No. 202180092514.2, dated Feb. 5, 2024, in 8 pages.

(Continued)

*Primary Examiner* — Yashita Sharma
*Assistant Examiner* — Jihad Dakkak
(74) *Attorney, Agent, or Firm* — PROCOPIO, CORY, HARGREAVES & SAVITCH LLP

(57) ABSTRACT

A monitoring apparatus is to be applied to an assisted circulation apparatus, the assisted circulation apparatus being connected to a living body, transferring blood removed from the living body to a membrane lung by a blood transfer pump, and gas-exchanging and oxygenating the blood in the membrane lung in parallel with a native lung, and the monitoring apparatus includes a calculation unit that calculates a blood gas-exchanging state index indicating a gas-exchanging state of blood by the assisted circulation apparatus.

6 Claims, 9 Drawing Sheets

(52) U.S. Cl.
CPC ............... *A61M 2205/3303* (2013.01); *A61M 2205/3327* (2013.01); *A61M 2205/50* (2013.01); *A61M 2230/205* (2013.01); *A61M 2230/432* (2013.01)

(58) Field of Classification Search
CPC .. A61M 2205/3303; A61M 2205/3327; A61M 2205/50; A61M 2230/205; A61M 2230/432
See application file for complete search history.

(56) References Cited

FOREIGN PATENT DOCUMENTS

| | | |
|---|---|---|
| CN | 111818951 A | 10/2020 |
| CN | 111905170 A | 11/2020 |
| JP | 2009-183617 A | 8/2009 |
| JP | 4562490 B2 | 10/2010 |
| JP | 2017-518106 A | 7/2017 |
| JP | 2018-139946 A | 9/2018 |
| JP | 2020-014729 A | 1/2020 |
| WO | 2011/021978 A1 | 2/2011 |
| WO | 2018/106164 A1 | 6/2018 |
| WO | 2019/155365 A1 | 8/2019 |

OTHER PUBLICATIONS

International Search Report, with translation, and Written Opinion received in corresponding International Application No. PCT/JP2021/04434, dated Mar. 1, 2022, in 11 pages.
Office Action received in corresponding TW Application No. 110145108, mailed Mar. 6, 2024, in 6 pages, with translation of Search Report.
International Search Report, with translation, and Written Opinion received in corresponding International Application No. PCT/JP2021/044342, dated Mar. 1, 2022, in 11 pages.
Notice of Allowance received in related CN App. No. 202180092514.2, issued Jul. 16, 2024, in 10 pages, with translation.
European Patent Office, Extended European Search Report, Application No. 21900681.4, dated Sep. 25, 2024, in 11 pages.

* cited by examiner

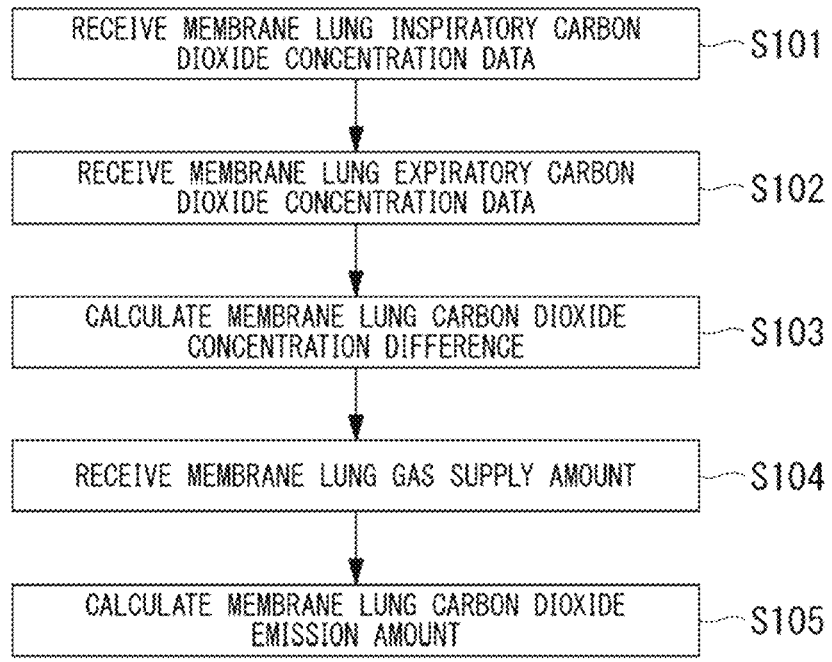
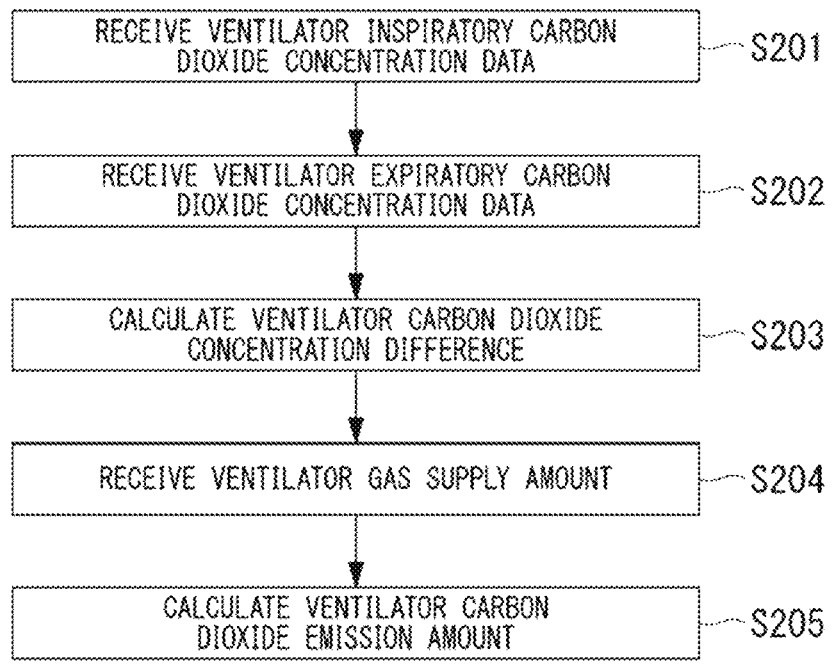

MONITORING APPARATUS AND ASSISTED CIRCULATION APPARATUS

TECHNICAL FIELD

The present invention relates to a monitoring apparatus connected to a living body and used to grasp the dynamics of assisted circulation, and an assisted circulation apparatus including it.

This application is a U.S. national stage application of International Application PCT/JP2021/044342, filed Dec. 2, 2021, which claims benefit to Japanese Patent Application No. 2020-200580, filed Dec. 2, 2020, the content of which is incorporated herein by reference.

BACKGROUND ART

As is well known, in cardiac surgery or the like, cardiopulmonary bypass (CPB) is performed to suspend the heart or bring it an approximately suspended state as necessary using an extracorporeal blood circulation apparatus.

In such cardiopulmonary bypass (CPB), gas exchange of blood is performed by a membrane lung (hereinafter, may be referred to as "ML").

In the cardiopulmonary bypass (CPB), for example, a monitoring apparatus used to grasp whether or not the gas exchange of blood by the membrane lung (ML) is appropriately performed has been developed (for example, refer to Patent Document 1).

On the other hand, when treating an acute pneumonia patient (ARDS), functional deterioration of a native lung (hereinafter, may be referred to as "NL") may be restored using a ventilator.

When using the ventilator, lung ventilation by the ventilator does not only sufficiently function due to the functional deterioration of the native lung (NL), but the native lung function may also decrease by using the operation of the ventilator.

Accordingly, in the treatment for the acute pneumonia patient (ARDS), the native lung function may be partially suspended, and the gas exchange of blood may be performed by assisted circulation (ExtraCorporeal Membrane Oxygenation, hereinafter referred to as "ECMO") in order to compensate for the functional deterioration of the native lung (NL).

Specifically, the membrane lung (ML) and the native lung (NL) are used together, and by performing gas exchange in the membrane lung (ML) on blood removed from the patient and returning the blood into the human body again, the function of the native lung (NL) is assisted by the membrane lung (ML).

The treatment by such assisted circulation (ECMO) may be performed for a long period of time, for example, from several days to a month, and the burden on health care workers tends to increase.

CITATION LIST

Patent Document

[Patent Document 1] Japanese Patent No. 4562490

SUMMARY OF INVENTION

Problem to be Solved by the Invention

However, when the gas exchange of blood is performed by the assisted circulation (ECMO), since the gas exchange of blood is not only performed in the membrane lung (ML) but is also performed in the native lung (NL), it is not easy to grasp whether or not the gas exchange of blood is appropriately performed by the assisted circulation (ECMO).

The management of the native lung (NL) by the ventilator relies on the monitoring for the ventilation amount, the end expiratory carbon dioxide partial pressure and the like, and it is difficult to control every respiration of the patient (living body) having the gas exchange of blood performed by using the assisted circulation (ECMO).

Therefore, in the treatment using the assisted circulation (ECMO), by intermittently blood gas-analyzing the blood collected from the patient and controlling whether or not the gas exchange of blood in the living body is appropriate, it is necessary to grasp whether or not the gas exchange of blood by the assisted circulation (ECMO) and every respiration of the patient by the native lung (NL) and the membrane lung (ML) are appropriately performed. Accordingly, it is a heavy burden on health care workers.

The present invention is made in consideration of the above circumstances, and an object thereof is to provide a monitoring apparatus capable of accurately grasping the gas-exchanging state of blood in a patient connected with an assisted circulation apparatus, and the assisted circulation apparatus including it.

Means to Solve the Problem

In order to solve the above problems, the present invention proposes the following means.

(1) A first aspect of the present invention is a monitoring apparatus for being applied to an assisted circulation apparatus, the assisted circulation apparatus being connected to a living body, transferring blood removed from the living body to a membrane lung by a blood transfer pump, and gas-exchanging and oxygenating the blood in the membrane lung in parallel with a native lung, and the monitoring apparatus includes; a calculation unit that calculates a blood gas-exchanging state index indicating a gas-exchanging state of blood by the assisted circulation apparatus.

According to the monitoring apparatus pertaining to the first aspect of the present invention, the blood gas-exchanging state index indicating a gas-exchanging state of blood in the native lung and the gas-exchanging state of blood by the assisted circulation apparatus can be calculated by the calculation unit.

As a result, the gas-exchanging state of blood in the native lung and the membrane lung can be accurately grasped.

In the present description, the blood gas-exchanging state index includes, for example, an index indicating a blood-oxygenated state (hereinafter, may be referred to as blood-oxygenated state index) and an index indicating a gas-exchanging amount (hereinafter, may be referred to as gas exchange index) at the time of oxygenating blood.

As the blood-oxygenated state index, well-known parameters such as the oxygen saturation degree in the membrane lung, the oxygen saturation degree in the living body, further, the hemoglobin concentration of blood, and the oxygen partial pressure of blood may be applied.

As the gas exchange index, well-known parameters such as the oxygen uptake amount in the membrane lung or the native lung, further, the carbon dioxide emission amount in the membrane lung or the native lung, the oxygen concentration (oxygen content, oxygen partial pressure) of gas capable of calculating them, the carbon dioxide concentration (carbon dioxide content, carbon dioxide partial pressure) thereof, and the gas supply amount thereof may be applied. Instead of the oxygen concentration, the carbon dioxide concentration and the like, a partial pressure of known respiratory gas (for example, anesthesia gas or the like) and the gas supply amount thereof, and the like may be applied.

When obtaining the gas exchange index (for example, the oxygen uptake amount) for oxygenating blood in the native lung, for example, respiratory gas using a ventilator, further, for example, the oxygen concentration of respiratory gas in natural breathing (for example, a case of using an oxygen mask) may be applied.

For example, the carbon dioxide ($CO_2$) concentration and the oxygen ($O_2$) concentration may be referred to as an oxygen content rate parameter as a parameter related to the gas content for oxygenating blood.

(2) In the monitoring apparatus according to (1) above, the calculation unit may calculate the blood gas-exchanging state index based on a gas-exchanging amount of blood in the membrane lung.

According to the monitoring apparatus pertaining to the present invention, the calculation unit calculates the blood gas-exchanging state index indicating the gas-exchanging state of blood by the assisted circulation apparatus based on the gas-exchanging amount of blood in the membrane lung, so the gas-exchanging state of blood by the membrane lung can be accurately grasped.

(3) In the monitoring apparatus according to (2) above, the calculation unit may calculate the gas-exchanging amount of blood in the membrane lung based on at least one of a carbon dioxide emission amount in the membrane lung and an oxygen uptake amount in the membrane lung.

According to the monitoring apparatus pertaining to the present invention, the calculation unit calculates the gas-exchanging amount of blood in the membrane lung based on at least one of the carbon dioxide emission amount in the membrane lung and the oxygen uptake amount in the membrane lung, so the gas-exchanging amount of blood in the membrane lung can be efficiently and accurately calculated.

As a result, the gas-exchanging state of blood by the membrane lung can be accurately grasped.

The phrase "at least one of the carbon dioxide emission amount and the oxygen uptake amount in the membrane lung" may denote that either one or both of the carbon dioxide emission amount and the oxygen uptake amount in the membrane lung. Another index that can be used to calculate the carbon dioxide emission amount and the oxygen uptake amount may be calculated.

When calculating the carbon dioxide emission amount and the oxygen uptake amount in the membrane lung, it is appropriate that, for example, the carbon dioxide content, the oxygen content, and the gas flow rate of the inspiratory gas and the expiratory gas of the membrane lung are obtained and the calculation is performed using them.

(4) In the monitoring apparatus according to (3) above, the calculation unit may calculate the carbon dioxide emission amount in the membrane lung by inspiratory gas and expiratory gas of the membrane lung.

According to the monitoring apparatus pertaining to the present invention, the calculation unit calculates the carbon dioxide emission amount in the membrane lung based on the inspiratory gas and the expiratory gas of the membrane lung input thereinto, so the carbon dioxide emission amount in the membrane lung can be accurately calculated.

As a result, the oxygen uptake amount in the membrane lung can be appropriately grasped.

The carbon dioxide emission amount in the membrane lung can be calculated by, for example, the following expression.

(the carbon dioxide ($CO_2$) emission amount of the membrane lung emission) $V'CO_2(ML)$=(the membrane lung expiratory average gas carbon dioxide ($CO_2$) concentration)×(the membrane lung expiratory gas flow rate)−(the membrane lung inspiratory average gas carbon dioxide ($CO_2$) concentration)×(the membrane lung inspiratory gas flow rate)

The carbon dioxide emission amount in the membrane lung may be calculated (approximated) by the following expression.

(the carbon dioxide ($CO_2$) emission amount of the membrane lung emission) $V'CO_2(ML)$=(the membrane lung expiratory average carbon dioxide ($CO_2$) concentration−the membrane lung inspiratory average carbon dioxide ($CO_2$) concentration)×(the membrane lung inspiratory gas flow rate)

When calculating the carbon dioxide emission amount using these expressions, it is appropriate that compensation is performed using temperature, pressure, or the like.

(5) In the monitoring apparatus according to any one of (1) to (4) above, the calculation unit may calculate the blood gas-exchanging state index based on a gas-exchanging amount of blood in the native lung.

According to the monitoring apparatus pertaining to the present invention, the calculation unit calculates the blood gas-exchanging state index in the native lung, so the gas-exchanging state of blood by the native lung can be accurately grasped.

(6) In the monitoring apparatus according to (5) above, the calculation unit may calculate the gas-exchanging amount of blood in the native lung based on at least one of a carbon dioxide emission amount in the native lung and an oxygen uptake amount in the living body.

According to the monitoring apparatus pertaining to the present invention, the calculation unit calculates the gas-exchanging amount of blood in the native lung based on at least one of the carbon dioxide emission amount in the native lung and the oxygen uptake amount in the native lung, so the gas-exchanging amount of blood in the native lung can be efficiently and accurately calculated.

As a result, the oxygenation status of blood by the native lung can be grasped.

The phrase "at least one of the carbon dioxide emission amount and the oxygen uptake amount in the native lung" denotes the same as in the membrane lung.

(7) In the monitoring apparatus according to (6) above, the calculation unit may calculate the carbon dioxide emission amount in the native lung by inspiratory gas and expiratory gas of the native lung.

According to the monitoring apparatus pertaining to the present invention, the calculation unit calculates the carbon dioxide emission amount in the native lung based on the inspiratory gas and the expiratory gas of the native lung input thereinto, so the carbon dioxide emission amount in the native lung can be accurately calculated.

As a result, the oxygenation status of blood by the native lung can be grasped.

The carbon dioxide emission amount in the native lung is appropriately calculated by, for example, the following expression.

the carbon dioxide ($CO_2$) emission amount by the native lung $V'CO_2(NL)$=(the native lung expiratory average carbon dioxide ($CO_2$) concentration)×(the native lung expiratory gas flow rate)−
(the native lung inspiratory average carbon
dioxide ($CO_2$) concentration)×(the native lung
inspiratory gas flow rate)

When calculating the carbon dioxide ($CO_2$) emission amount by the native lung, for example, the respiratory gas concentration (oxygen concentration, carbon dioxide concentration) in the ventilator may be applied.

(8) In the monitoring apparatus according to (6) or (7) above, the calculation unit may calculate the carbon dioxide emission amount in the native lung by volume capno analysis.

According to the monitoring apparatus pertaining to the present invention, the calculation unit calculates the carbon dioxide emission amount in the native lung by generally applicable volume capno analysis, so the carbon dioxide emission amount in the native lung can be efficiently and accurately calculated.

(9) In the monitoring apparatus according to any one of (5) to (8) above, the calculation unit may calculate a contribution degree of assisted circulation to gas exchange of blood of the living body based on a gas-exchanging amount of blood in the membrane lung and the gas-exchanging amount in the native lung.

According to the monitoring apparatus pertaining to the present invention, the calculation unit calculates the contribution degree of the assisted circulation to the gas exchange of blood of the living body based on the gas-exchanging amount of blood in the membrane lung and the gas-exchanging amount in the native lung, so the gas-exchanging state of blood by the assisted circulation in the living body can be accurately grasped.

The contribution degree by the assisted circulation to the gas exchange of blood in the living body may be expressed by, for example, an assisted circulation ratio (ECMO Rate).

The assisted circulation ratio (ECMO Rate) can be calculated by the following expressions.

the assisted circulation ratio (ECMO Rate)=(the carbon dioxide ($CO_2$) emission amount of the membrane lung (ML)/(the total emission amount of carbon dioxide ($CO_2$) generated in the whole living body)

(the total emission amount of carbon dioxide ($CO_2$) generated in the whole living body)=(the carbon dioxide ($CO_2$) emission amount by the lung function of the native lung)+(the carbon dioxide ($CO_2$) emission amount by the membrane lung)

The expressing of the contribution degree by the assisted circulation to the gas exchange of blood in the living body is not limited to the assisted circulation ratio (ECMO Rate, percentage) and can be arbitrarily set, and for example, various indexes indicating a contribution by the assisted circulation to the gas exchange, such as a ratio of the gas-exchanging amount of the membrane lung to the gas-exchanging amount of the native lung, may be applied.

(10) In the monitoring apparatus according to (9) above, the calculation unit may calculate the contribution degree of assisted circulation by a ratio of the gas-exchanging amount of blood in the membrane lung to a total of the gas-exchanging amount of blood in the membrane lung and the gas-exchanging amount in the native lung.

According to the monitoring apparatus pertaining to the present invention, the calculation unit calculates the contribution degree of the assisted circulation by the ratio (assisted circulation ratio (ECMO Rate)) of the gas-exchanging amount of blood in the membrane lung to the gas-exchanging amount of blood in the membrane lung and the gas-exchanging amount in the native lung, so the contribution degree can be easily and efficiently calculated.

(11) in the monitoring apparatus according to any one of (1) to (10) above, the calculation unit may calculate a contribution degree of assisted circulation to the living body based on a blood-oxygenated state index indicating an oxygenation state of blood by the membrane lung and a blood-oxygenated state index indicating an oxygenation state of blood in the living body.

According to the monitoring apparatus pertaining to the present invention, the calculation unit calculates the contribution degree of the assisted circulation to the living body based on the blood-oxygenated state index by the membrane lung and the blood-oxygenated state index in the living body, so the contribution degree can be easily and efficiently calculated.

(12) In the monitoring apparatus according to (11) above, the calculation unit may compare a gas exchange index in the living body with a blood-oxygenated state index based on metabolism estimated from a weight of the living body.

According to the monitoring apparatus pertaining to the present invention, the calculation unit compares the gas exchange index in the living body with the blood-oxygenated state index based on the metabolism estimated (calculated) from the weight of the living body, so it is possible to efficiently grasp whether or not the oxygenation of blood in the whole living body is appropriately performed.

As the gas exchange index in the living body, for example, the total emission amount of carbon dioxide ($CO_2$) generated in the whole living body may be applied.

As an example of the blood-oxygenated state index based on the metabolism estimated (calculated) from the weight of the living body, the carbon dioxide ($CO_2$) amount due to metabolism assumed at rest shown below may be applied.

[the carbon dioxide ($CO_2$) amount due to metabolism assumed at rest] = [1 $METs$] × 0.8 × [the weight of the living body (patient) $P$]

evaluation of exercise intensity: METs (MET: metabolic equivalent)

1 METs is indicated by the oxygen uptake amount at rest (3.5 mil/kg/min). The constant 0.8 is the respiratory quotient.

(13) in the monitoring apparatus according to any one of (1) to (12) above, the calculation unit may calculate at set time intervals.

According to the monitoring apparatus pertaining to the present invention, the calculation unit calculates at set time intervals, so the dynamics of the assisted circulation (ECMO) with respect to the entire respiratory metabolism of the living body can be grasped as a trend.

By accumulating data in chronological order, the dynamics of the assisted circulation (ECMO) can be accurately grasped.

The set time interval may be manually set or may be automatically set so as to correspond to the interval time measured by a sensor or the like, and can be arbitrarily set. It may be calculated and displayed in real time or with a certain time delay.

(14) A second aspect of the present invention is an assisted circulation apparatus including the monitoring apparatus according to any one of (1) to (13) above.

Effects of the Invention

According to a monitoring apparatus pertaining to the present invention, the gas-exchanging state of blood in a living body connected with an assisted circulation apparatus.

BRIEF DESCRIPTION OF THE DRAWINGS

FIG. 5 is a flowchart showing an outline of a calculating procedure in a membrane lung carbon dioxide emission calculation unit for showing the schematic configuration of the monitoring apparatus pertaining to the first embodiment.

FIG. 6 is a flowchart showing an outline of a calculating procedure in a ventilator carbon dioxide emission calculation unit for showing the schematic configuration of the monitoring apparatus pertaining to the first embodiment.

DESCRIPTION OF EMBODIMENTS

First Embodiment

Hereinafter, an assisted circulation (V-V ECMO) pertaining to a first embodiment of the present invention is described with reference to FIGS. 1 to 9.

Figure 1:
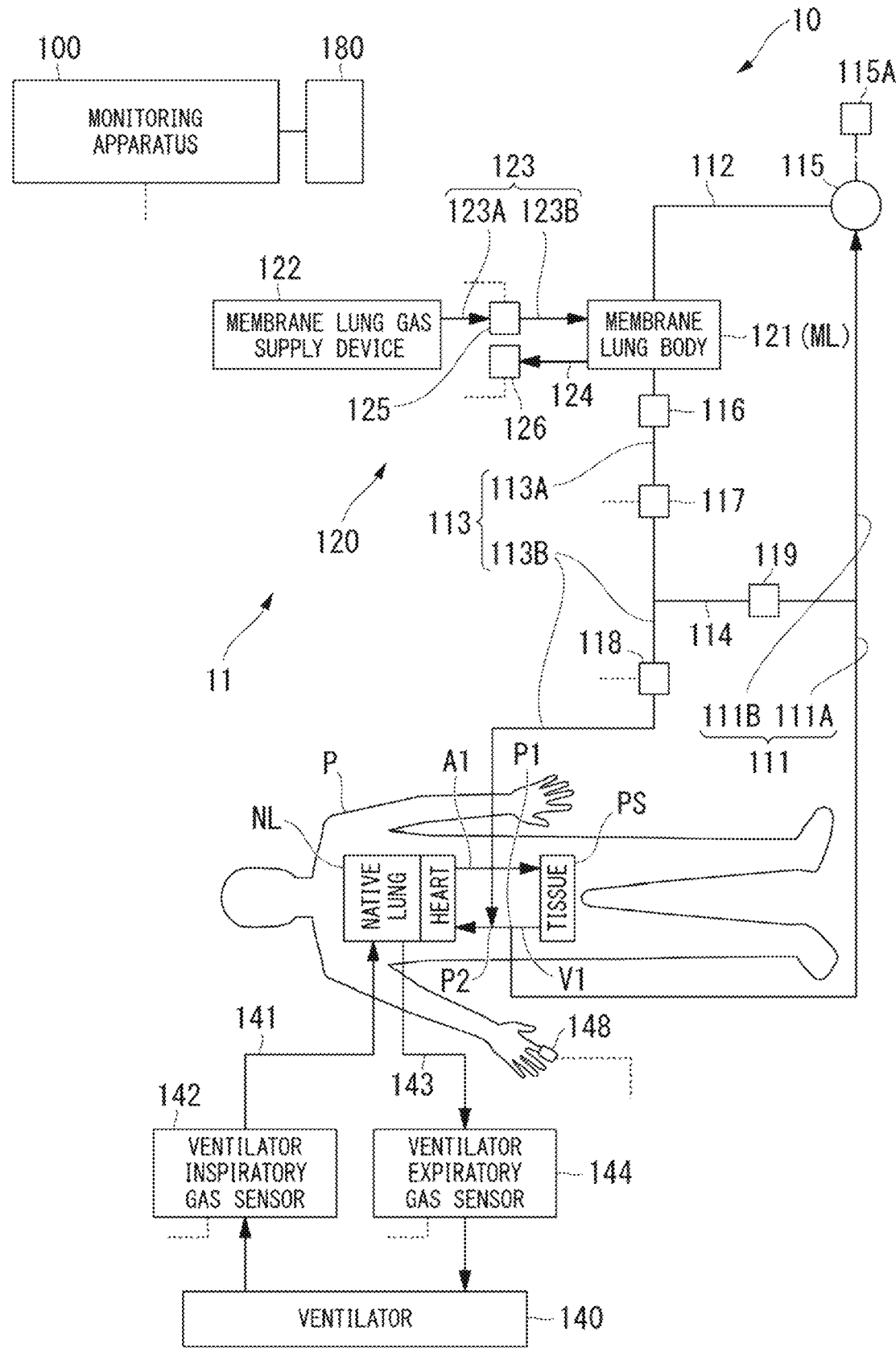
FIG. 1 is a conceptual diagram showing a schematic configuration of an assisted circulation (V-V ECMO) pertaining to a first embodiment of the present invention.

FIG. 1 is a conceptual diagram showing a schematic configuration of the assisted circulation (V-V ECMO) pertaining to the first embodiment. The dotted lines shown in FIG. 1 simplify and denote electric cables connecting sensors and a monitoring apparatus 100. That is, the monitoring apparatus 100 is connected to sensors and the like 117, 118, 125, 126, 142, 144 and 148 described below through the electric cables or wireless communication and is configured so as to obtain information from these sensors by wire or wirelessly.

In FIG. 1, a reference sign 10 represents an assisted circulation system (blood circulation circuit) in the assisted circulation (V-V ECMO), a reference sign 100 represents the monitoring apparatus, a reference sign 115 represents a centrifugal pump (blood transfer pump), a reference sign 120 represents a membrane lung, a reference sign 140 represents a ventilator, a reference sign 148 represents a pulse oximeter (blood oxygenation index-measuring device), and a reference sign 180 represents an LCD touch panel.

Hereinafter, the assisted circulation system (blood circulation circuit) is referred to as an assisted circulation system (V-V ECMO).

The first embodiment is an example in which as shown in FIG. 1, a patient (living body) is connected with, for example, the assisted circulation system (V-V ECMO) 10 and the ventilator 140.

In the first embodiment, as shown in FIG. 1, the patient (living body) P is connected with, for example, the monitoring apparatus 100, the assisted circulation system (V-V ECMO) 10, the LCD touch panel 180, the ventilator 140, and the pulse oximeter (blood oxygenation index-measuring device) 148. The monitoring apparatus 100 is connected to the patient P through sensors. The LCD touch panel 180 of the present embodiment is connected to the monitoring apparatus 100.

As shown in FIG. 1, the assisted circulation system (V-V ECMO) 10 is configured such that blood removed from a vein V1 of the patient (living body, human body) P is circulated by the centrifugal pump (blood transfer pump) 115, the blood is gas-exchanged in the membrane lung 120 and is returned to the vein V1 of the patient P again.

The patient (living body, human body) P is connected with the ventilator 140 and inhales inspiratory gas supplied from the ventilator 140, and artificial respiration in which blood is oxygenated in the native lung (NL) thereof is performed.

As shown in FIG. 1, the assisted circulation system (V-V ECMO) 10 includes, for example, a blood removal line 111, a blood transfer line 112, a blood return line 113, a recirculation line 114, the centrifugal pump (blood transfer pump) 115, a flow sensor 116, the oxygen saturation sensor 117, the blood transfer auto clamp 118, a recirculation clamp 119, and the membrane lung 120.

In the present embodiment, of the configuration of the assisted circulation system 10, the flow sensor 116, the oxygen saturation sensor 117, the blood transfer auto clamp 118, the recirculation clamp 119, and the membrane lung 120 configure an assisted circulation apparatus 11. In other words, the assisted circulation system 10 includes the assisted circulation apparatus 11, the blood removal line 111, the blood transfer line 112, the blood return line 113, the recirculation line 114, and the centrifugal pump 115, and the components 111, 112, 113, 114 and 113 can be handled as disposable products.

It is sufficient that the minimum configuration of the assisted circulation apparatus 11 includes the flow sensor 116, the oxygen saturation sensor 117, the blood transfer auto clamp 118, the recirculation clamp 119, and the membrane lung 120, and the assisted circulation apparatus 11 may be configured to include other components (for example, part of the above lines). The assisted circulation apparatus 11 may further include a drive unit 115A that drives the centrifugal pump 115. The drive unit 115A includes, for example, a motor such as an AC servomotor or a DC servomotor as a drive source for the centrifugal pump 115. The drive unit 115A may include a controller configured of a processor or an integrated circuit (IC) which controls the motor. The assisted circulation apparatus 11 may further include the monitoring apparatus 100.

As shown in FIG. 1, for example, the blood removal line 111, the centrifugal pump 115, the blood transfer line 112, a membrane lung body 121, and the blood return line 113 are arranged in this order with respect to the patient P, and the blood removed from the patient P circulates in this order and returns to the patient P in a steady state.

The blood removal line 111 includes, for example, a first blood removal line 111A connected to the upstream side (the patient P), and a second blood removal line 111B connected to the downstream side (the centrifugal pump). The blood removal line 111 transfers the blood removed from the patient P to the centrifugal pump 115.

The blood transfer line 112 transfers blood sent out front, for example, the centrifugal pump 115 to the membrane lung 120.

The blood return line 113 includes, for example, a first return line 113A connected to the upstream side (the membrane lung), and a second return line 113B connected to the downstream side (the patient P).

The return line 113 transfers (returns) blood sent out from the membrane lung 120 to the vein V1 of the patient (living body) P.

The flow sensor 116 is disposed in the first return line 113.

The recirculation line 114 connects two points together, for example, one of the two points is between the first return line 113A and the second return line 113B of the blood return line 113, and the other of the two points is between the first blood removal line 111A and the second blood removal line 111B of the blood removal line 111.

The blood removal line 111, the blood transfer line 112, the return line 113, and the recirculation line 114 are formed of tubes made from, for example, flexible resin material.

As shown in FIG. 1, the centrifugal pump (blood transfer pump) 115 has an inflow side connected to the blood removal line 111 and an outflow side connected to the blood transfer line 112, makes impeller blades rotate by, for example, the AC servomotor or the DC servomotor, suctions blood removed from the patient P through the blood removal line 111, and transfers the blood to the membrane lung 120 through the blood transfer line 112.

The centrifugal pump 115 is configured so as to perform, for example, feedback control using a flow rate (flow speed) detected by the flow sensor 116 by operating a flow rate-setting switch (not shown).

As shown in FIG. 1, the blood transfer auto clamp 118 is disposed in, for example, the return line 113. Specifically, the blood transfer auto clamp 118 is disposed in the second return line 113B and is configured to close and open itself (i.e., the second return line 113B) by a clamping portion through, for example, manually operating an actuator.

The blood transfer auto clamp 118 is connected to the monitoring apparatus 100 by wire or wirelessly and transmits signals indicating the closed state of the blood transfer auto clamp 118 to the monitoring apparatus 100.

As shown in FIG. 1, the recirculation clamp 119 is disposed in, for example, the recirculation line 114 and is configured to close and open the recirculation line 114 by operating a clamping portion by, for example, a manually operated actuator.

When the blood transfer auto clamp 118 opens the second return line 113B, the recirculation clamp 119 closes the recirculation line 114, and the removed blood is circulated to the patient P through the blood removal line 111, the blood transfer line 112, and the return line 113 without through the recirculation line 114.

For example, in an emergency or the like, when the blood transfer auto clamp 118 closes the second return line 113B, the blood flow in the second return line 113B stops, but the recirculation clamp 119 opens the recirculation line 114, and the removed blood is circulated through the second blood removal line 111B, the blood transfer line 112, the first return line 113A, and the recirculation line 114. Thereby, even if gas supply to the membrane lung (ML) 120 is stopped, the blood circulates and does not stagnate, so blood coagulation can be prevented.

The oxygen saturation sensor (blood oxygenation index sensor) 117 includes, for example, a removed blood oxygen saturation sensor disposed in the second blood removal line 111B, and a returning blood oxygen saturation sensor disposed in the first return line 113A.

In FIG. 1, only the returning blood oxygen saturation sensor is represented by the reference sign 117 for the sake of simplicity.

In the present embodiment, the oxygen saturation sensor (returning blood oxygen saturation sensor) 117 is connected to the monitoring apparatus 100 by cables (not shown), detects the oxygen saturation degree and hemoglobin amount of blood sent out from the membrane lung body 121 and flowing in the first return line 113A, and transmits them to the monitoring apparatus 100.

In the present embodiment, the oxygen saturation sensor 117 is configured so as to detect the oxygenation index (oxygenation degree, blood oxygenation index) of hemoglobin in blood by infrared radiation, for example.

The configuration of the oxygen saturation sensor 117 can be arbitrarily set as long as the degree of blood oxygenation can be detected, and known various sensors capable of measuring the blood oxygenation index may be applied thereto.

As shown in FIG. 1, the membrane lung 120 includes, for example, the membrane lung body 121, a membrane lung inspiratory line 123, a membrane lung expiratory line 124, the membrane lung inspiratory gas sensor 125, and the membrane lung expiratory gas sensor 126 and is connected to a membrane lung gas supply device 122.

The membrane lung 120 is configured to oxygenate the blood flowing through the assisted circulation system (V-V ECMO) 10.

The membrane lung body 121 includes, for example, a hollow fiber membrane, a flat membrane or the like having excellent gas permeability.

The membrane lung body 121 is configured such that in the hollow fiber membrane, the flat membrane or the like, oxygen of the supplied gas moves to the blood, and carbon dioxide dissolved in the blood moves to the gas supplied to the membrane lung, thereby gas-exchanging the blood. The membrane lung body 121 is integrated with, for example, a heat exchanger for adjusting the temperature of blood.

The configuration of the membrane lung body 121 can be arbitrarily set as long as the gas exchange of blood can be performed.

The membrane lung gas supply device 122 supplies gas having an oxygen ($O_2$) concentration adjusted to be suitable for the gas exchange to the membrane lung body 121. In the present embodiment, for example, the oxygen ($O_2$) concentration of the gas is adjusted to 100%.

The membrane lung inspiratory line 123 includes, for example, a first inspiratory line 123A connected to the membrane lung gas supply device 122, and a second inspiratory line 123H connected to the membrane lung body 121.

The membrane lung inspiratory line 123 transfers the membrane lung inspiratory gas sent out from the membrane lung gas supply device 122 to the membrane lung body 121.

The membrane lung expiratory line 124 releases the expiratory gas discharged from the membrane lung body 121 to the outside of the system.

The membrane lung inspiratory line 123 and the membrane lung expiratory line 124 are funned of tubes made from, for example, flexible resin material.

In the present embodiment, the membrane lung inspiratory gas sensor 125 is configured of, for example, a carbon dioxide ($CO_2$) sensor.

The membrane lung inspiratory gas sensor 125 is disposed in the membrane lung inspiratory line 123. Specifically, the membrane lung inspiratory gas sensor 125 is disposed between the first membrane lung inspiratory line 123A and the second membrane lung inspiratory line 123B.

The membrane lung inspiratory gas sensor 125 detects the carbon dioxide ($CO_2$) concentration (oxygen content parameter) of the inspiratory gas to be sent into the membrane lung body 121 through the membrane lung inspiratory line 123.

In the present embodiment, the membrane lung expiratory gas sensor 126 is configured of, for example, a carbon dioxide ($CO_2$) sensor.

The membrane lung expiratory gas sensor 126 is disposed in the membrane lung expiratory line 124. Specifically, the membrane lung expiratory gas sensor 126 is disposed at the downstream end of the membrane lung expiratory line 124.

The membrane lung expiratory gas sensor 126 detects the carbon dioxide ($CO_2$) concentration (oxygen content parameter) contained in the expiratory gas discharged from the membrane lung body 121 through the membrane lung expiratory line 124.

The configurations of the membrane lung inspiratory gas sensor 125 and the membrane lung expiratory gas sensor 126 can be arbitrarily set, and for example, oxygen ($O_2$) sensors may be applied thereto instead of the carbon dioxide ($CO_2$) sensors. Known various sensors may be applied to the membrane lung inspiratory gas sensor 125 and the membrane lung expiratory gas sensor 126 as long as the sensors can detect concentration parameters such as the partial pressure of carbon dioxide ($CO_2$), which are used to determine the carbon dioxide ($CO_2$) concentration of the inspiratory gas and the expiratory gas.

For example, it may be configured that a sampling circuit (not shown) is provided in the membrane lung inspiratory line 123 and the membrane lung expiratory line 124, the sampling line thereof is switched between the membrane lung inspiratory line 123 and the membrane lung expiratory line 124, and thereby one gas sensor operates as both of the membrane lung expiratory gas sensor 125 and the membrane lung expiratory gas sensor 126.

As shown in FIG. 1, the ventilator 140 is connected to the patient P through, for example, a ventilator inspiratory line 141 and a ventilator expiratory line 143.

The ventilator 140 is configured to supply ventilator gas having an increased oxygen ($O_2$) concentration to the patient (living body) P to assist efficient gas exchange of blood in the patient P.

Although the configuration of the ventilator 140 can be arbitrarily set, in the present embodiment, the ventilator 140 is configured to include, for example, a gas circuit, an inspiratory valve, an expiratory valve, a pressure-controlling circuit, a flow rate-controlling circuit, and a display unit, the gas circuit includes a pressure-reducing valve, and the display unit is also used as an input interface (I/O).

The ventilator inspiratory line 141 transfers ventilator inspiratory gas sent out from the ventilator 140 to the native lung (NL) of the patient P.

As shown in FIG. 1, for example, the ventilator inspiratory gas sensor 142 is disposed in the ventilator inspiratory line 141 and can detect the carbon dioxide ($CO_2$) concentration (oxygen content parameter) of the inspiratory gas to be supplied from the inspirator 140 through the ventilator inspiratory line 141 to the patient P.

The ventilator expiratory line 143 transfers the expiratory gas discharged from the native lung (NL) of the patient P to the ventilator 140.

As shown in FIG. 1, for example, the ventilator expiratory gas sensor 144 is disposed in the ventilator expiratory line 143 and can detect the carbon dioxide (CO)) concentration (oxygen content parameter) of the expiratory gas after the oxygenation of blood discharged from the patient P and to be transferred to the ventilator 140 through the ventilator expiratory line 143.

Hereinafter, the operation of the assisted circulation system (V-V ECMO) is described with reference to FIGS. 1, 2 and 3.

Figure 2:
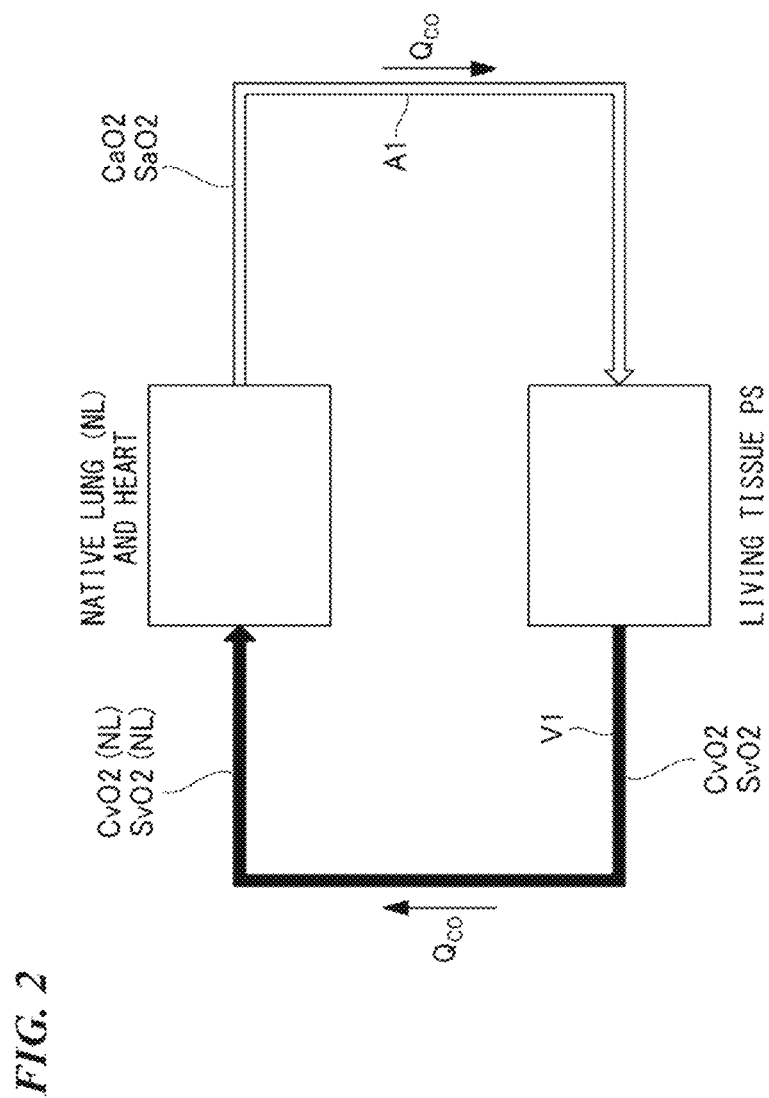
FIG. 2 is a conceptual diagram showing an overview of blood circulation of a patient without the assisted circulation (V-V ECMO) pertaining to the first embodiment applied thereto.
Figure 3:
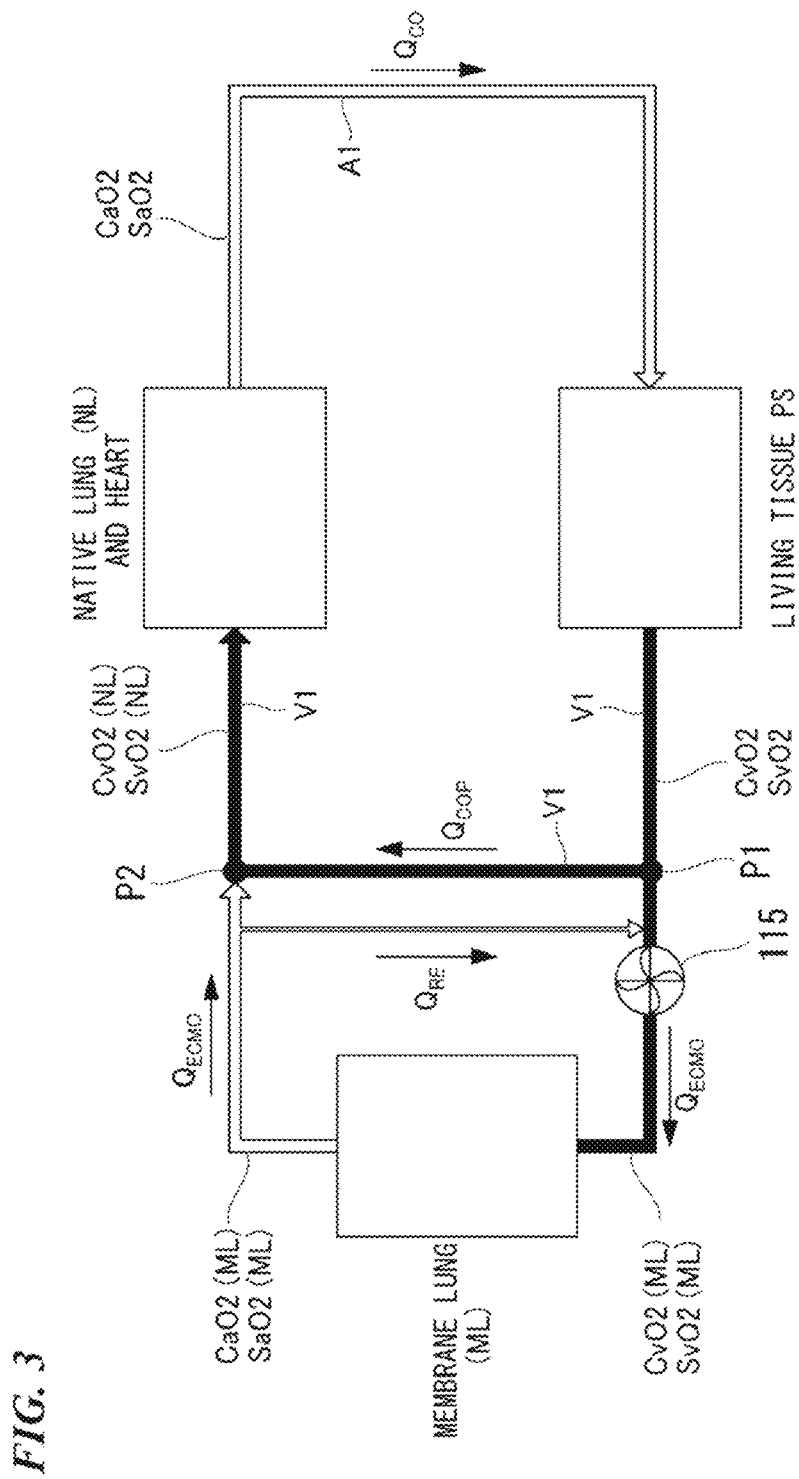
FIG. 3 is a conceptual diagram showing an overview of blood circulation of a patient having the assisted circulation (V-V ECMO) pertaining to the first embodiment applied thereto.

FIG. 2 is a conceptual diagram showing an overview of blood circulation of a patient (living body) P without the assisted circulation system (V-V ECMO) applied thereto, and FIG. 3 is a conceptual diagram showing an overview of blood circulation of a patient P having the assisted circulation system (ECMO) applied thereto. In FIGS. 2 and 3, a blood flow between the heart and the native lung is omitted.

In FIGS. 2 and 3, white arrows indicate the flow of blood after the gas exchange, and filled arrows indicate the flow of blood before the gas exchange.

[Case of not Applying Assisted Circulation System (ECMO)]

First, with reference to FIG. 2, the blood circulation in a case where the assisted circulation system (ECMO) is not applied is described.

When the assisted circulation system (ECMO) is not applied, in the blood circulation in the patient (living body) P, as shown in FIG. 2, blood having an oxygen content (oxygen content parameter) $CaO_2$ and an oxygen saturation degree (blood-oxygenated state index) $SaO_2$ after it is oxygenated in the native lung (NL) is sent out by the heart through an artery A1 to the living tissue PS of the whole body.

In the blood delivered to the living tissue PS, part of the oxygen ($O_2$) in the blood is consumed by metabolism, carbon dioxide ($CO_2$) is generated, and the oxygen content and the oxygen saturation degree thereof decrease to an oxygen content (oxygen content parameter) $CvO_2$ and an oxygen saturation degree (blood-oxygenated state index) $SvO_2$.

The blood returns to the heart and the native lung (NL) through the vein V1.

In this blood circulation, blood flows through the artery A1 and the vein V1 at, for example, an equal flow rate $Q_{CO}$.

[Case of Applying Assisted Circulation System (V-V ECMO) 10]

Next, with reference to FIG. 3, the blood circulation in a case where the assisted circulation system (ECMO) is applied is described.

In the patient (living body) P having the assisted circulation system (V-V ECMO) 10 applied thereto, as shown in FIG. 3, blood oxygenated in the native lung (NL) and having an oxygen content (oxygen content parameter) $CaO_2$, an oxygen saturation degree (blood-oxygenated state index) $SaO_2$, and a flow rate (cardiac output) $Q_{CO}$ is sent out by the heart through the artery A1 to the living tissue PS of the whole body.

Blood gas-exchanged (metabolized) in the living tissue PS and having an oxygen content (oxygen content parameter) $CvO_2$, an oxygen saturation degree (blood-oxygenated state index) $SvO_2$, and a flow rate (equivalent to the cardiac output) $Q_{CO}$ flows through the vein V1 toward the heart and the native lung, and blood with a flow rate $Q_{ECMO}$ is removed from a blood removal point P1 and flows to the membrane lung (ML) of the assisted circulation system (V-V ECMO) 10.

On the other hand, blood not removed from the blood removal point P and having a flow rate $Q_{COP}$ (=$Q_{CO}$−$Q_{ECMO}$) flows directly toward the heart through the vein V1.

$Q_{RE}$ shown in FIG. 3 denotes the flow rate of blood recirculated in the assisted circulation (V-V ECMO), which is oxygenated and returned to the vein V1 and thereafter flows into the membrane lung (ML) again.

The removed blood is sent to the membrane lung (ML), is gas-exchanged and oxygenated in the membrane lung (ML), and is returned to the vein V1 at a return point P2.

The blood returned to the vein V1 at the return point P2 is mixed with blood flowed through the vein V1 and having the oxygen content $CvO_2$ and the oxygen saturation degree $SvO_2$ to become blood having an oxygen content (oxygen content parameter) $CvO_2$ (NL), an oxygen saturation degree (blood-oxygenated state index) $SvO_2$ (NL), and the flow rate $Q_{CO}$ and to be delivered to the native lung (NL).

The blood is oxygenated in the native lung (NL) to become blood having the oxygen content $CaO_2$ and the oxygen saturation degree $SaO_2$, and is sent out to the artery A1.

At this time, the blood sent out to the artery A1 is oxygenated by, for example, an oxygen uptake amount V'$O_2$ (ML) in the membrane lung (ML) and is oxygenated by oxygen ($O_2$) having an oxygen uptake amount V'$O_2$ (NL) in the native lung (NL).

The contribution degree of the assisted circulation (ECMO) to the living body can be expressed by, for example, the following assisted circulation ratio (ECMO Rate).

For example, when the assisted circulation ratio (ECMO Rate) is expressed with a focus on the oxygen uptake amount, the following expression is obtained.

the assisted circulation ratio (ECMO Rate) =

(the oxygen uptake amount V'$O_2$(ML) in the membrane lung (ML))/

(the oxygen uptake amount V'$O_2$(ML) in the membrane lung (ML) + the oxygen uptake amount V'$O_2$(NL) in the native lung (NL))

That is, the contribution degree of the assisted circulation (ECMO) to the living body can be expressed by a ratio of the gas-exchanging amount of blood in the membrane lung (ML) to the total of the gas-exchanging amount of blood in the membrane lung (ML) and the gas-exchanging amount in the native lung (NL).

The oxygen uptake amount V'$O_2$ (NL) in the native lung (NL) can be obtained as the oxygen content contained in respiratory gas of the patient (living body).

When the assisted circulation ratio (ECMO Rate) is expressed with a focus on the carbon dioxide emission amount, the following expression is obtained.

the assisted circulation ratio (ECMO Rate) =

(the carbon dioxide emission amount V'$CO_2$(ML)

in the membrane lung (ML))/(the carbon dioxide emission amount V'$CO_2$(ML) in the membrane lung (ML) + the carbon dioxide emission amount V'$CO_2$(NL) in the native lung (NL))

The carbon dioxide emission amount V'$CO_2$ (NL) in the native lung (NL) can be obtained as the carbon dioxide content contained in respiratory gas of the patient (living body).

Regarding the blood circulation shown in FIG. 3, it is possible to confirm the gas-exchanging state of blood by calculating using, for example. Formulas [101] to (106) shown below.

First, Formula (101) shows the relationship between the oxygen uptake amount in the membrane lung (ML) and the native lung (NL) and the amount [$DaO_2$−$DvO_2$] of oxygen consumed in the living tissue.

[Expression 1]
$$V'O_2 = V'O_2(NL) + V'O_2(ML) = D_aO_2 - D_vO_2 \quad (101)$$

When transforming Formula (101), following Formula (102) holds.

[Expression 2]
$$D_aO_2 = V'O_2(NL) + V'O_2(ML) + D_VO_2 \quad (102)$$

The oxygen transfer rate $DvO_2$ of blood flowing through the vein V1 shown in FIG. 2 can be expressed by following Formula (103).

[Expression 3]
$$D_VO_2 = C_VO_2 \times Q_{CO} \quad (103)$$

The oxygen uptake amount in the membrane lung (ML) is $Q_{ECMO}$×(the oxygen content $CaO_2$ (ML) of blood oxygenated in the membrane lung (ML)−the oxygen content $CvO_2$ (ML) before being oxygenated in the membrane lung (ML)), so the oxygen content $CaO_2$ (ML) is expressed by following Formula (104).

[Expression 4]
$$C_aO_2(ML) = C_vO_2(ML) + \frac{V'O_2(ML)}{Q_{ECMO}} \quad (104)$$

When substituting Formula (104) for Formula (102), the blood oxygen transfer rate $DaO_2$ of the cardiac output flowing through the artery A1 is expressed as following Formula (105).

[Expression 5]

$$D_aO_2 = V'O_2(NL) + C_aO_2(ML) - C_vO_2(ML)) \times Q_{ECMO} + C_vO_2 \times Q_{CO} \quad (105)$$

The oxygen uptake amount $DaO_2$–$DvO_2$ in the membrane lung (ML) and the native lung (NL) corresponds to the oxygen uptake amount in the membrane lung (ML) and the native lung (NL). Since the oxygen uptake amount corresponds to the carbon dioxide emission amount, when focusing on the carbon dioxide emission amount, following Formula (106) is derived out. The oxygen uptake amount and the carbon dioxide emission amount are the gas exchange index of blood.

[Expression 6]

$$\frac{D_aO_2}{V'CO_2} = \frac{(C_aO_2(ML) - C_vO_2(ML)) \times Q_{EMCO} + C_vO_2 \times Q_{CO} + V'O_2(NL)}{V'O_2(NL) + V'O_2(ML)} \quad (106)$$

The monitoring apparatus 100 described below may appropriately calculate whether or not an index can be calculated by above Formulas (101) to (106), and it may be displayed on the LCD touch panel 180.

Figure 4:
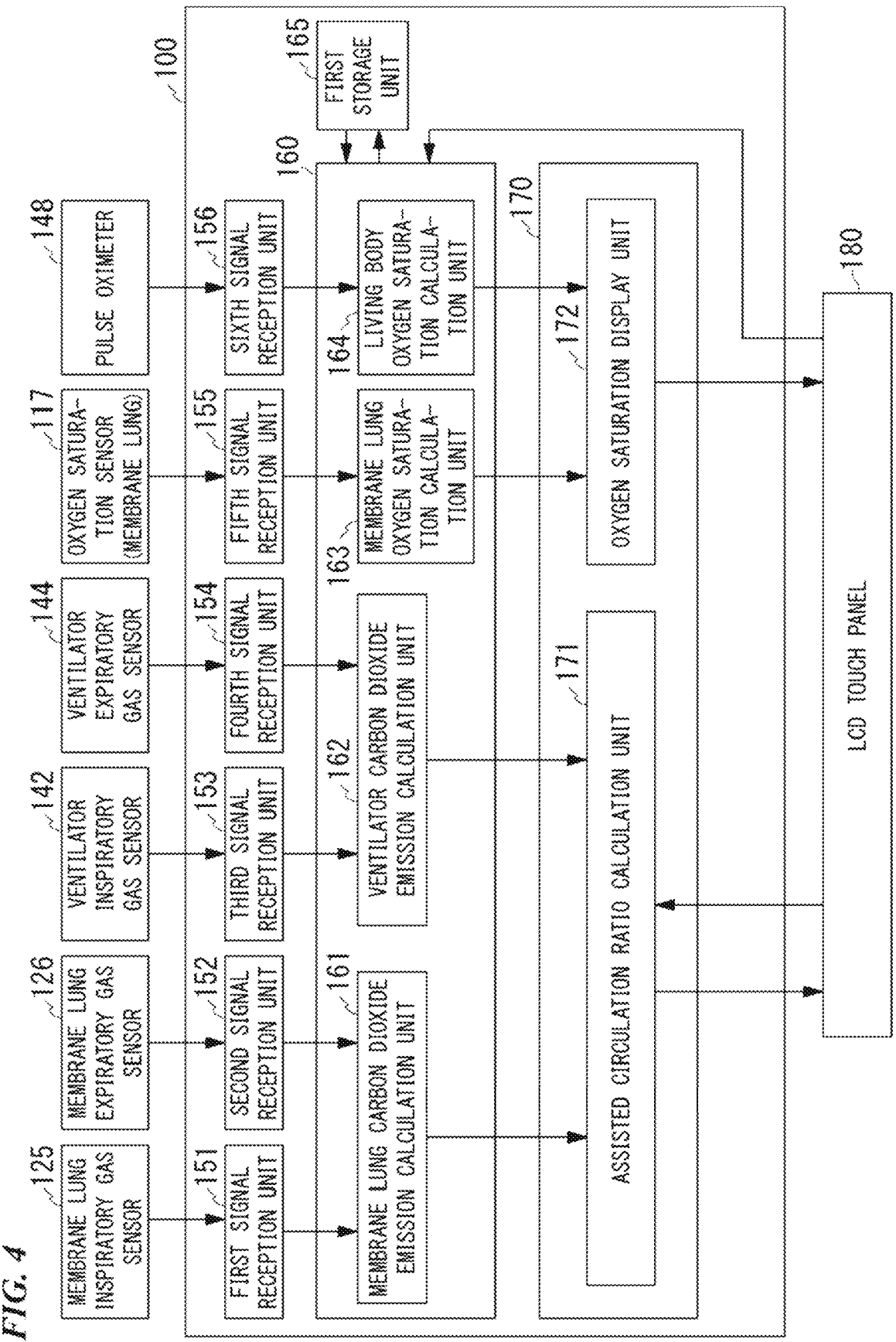
FIG. 4 is a block diagram showing a schematic configuration of a monitoring apparatus pertaining to the first embodiment.

Next, the schematic configurations of the monitoring apparatus 100 and the LCD touch panel 180 are described with reference to FIGS. 4 to 9. FIG. 4 is a block diagram showing the schematic configuration of the monitoring apparatus pertaining to the first embodiment. FIGS. 5 to 8 are flowcharts showing outlines of calculating procedures in the monitoring apparatus, and FIG. 9 is a conceptual diagram showing the schematic configuration of the LCD touch panel connected to the monitoring apparatus.

Although the configurations of the monitoring apparatus 100 and the LCD touch panel 180 can be arbitrarily set, in the present embodiment, the monitoring apparatus 100 can calculate the assisted circulation ratio (ECMO Rate) in the assisted circulation system (V-V ECMO) 10 and compare the oxygen saturation degree (blood-oxygenated state index) of blood of the patient (living body) P therewith.

As shown in FIG. 4, the monitoring apparatus 100 includes, for example, a first signal reception unit 151 to a sixth signal reception unit 156, a first calculation unit 160, a second calculation unit 170, and a first storage unit 165 and is configured so as to perform various calculations at set time intervals. The signal reception units 151 to 156 are, for example, input ports.

In the present embodiment (and a second embodiment described below), the monitoring apparatus 100 may be configured to include the first signal reception unit 151 to the sixth signal reception unit 156, the first calculation unit 160, and the second calculation unit 170 without including the first storage unit 165. That is, a component corresponding to the first storage unit 165 may be connected to the monitoring apparatus 100 by wire or wirelessly, and they may be configured to transmit and receive information therebetween. The monitoring apparatus 100 may also be configured to include the LCD touch panel 180.

In the present embodiment, the monitoring apparatus 100 is configured to calculate using signals input from the sensors in real time and output the results.

As shown in FIG. 4, the monitoring apparatus 100 is connected to the membrane lung inspiratory gas sensor 125, the membrane lung expiratory gas sensor 126, the ventilator inspiratory gas sensor 142, the ventilator expiratory gas sensor 144, the oxygen saturation sensor 117, and the pulse oximeter 148 through cables and is configured such that signals are appropriately input thereinto from them. The monitoring apparatus 100 may be configured so as to obtain information measured by at least one of the sensors 117, 125, 126, 142, 144 and 148 through wireless communication without through cables. The monitoring apparatus 100 may include a receiver that receives information measured by the sensors.

The first signal reception unit 151 is connected to the membrane lung inspiratory gas sensor 125 and is configured to receive a membrane lung inspiratory carbon dioxide ($CO_2$) concentration (oxygen content parameter) signal indicating the carbon dioxide concentration contained in membrane lung inspiratory gas, which is sent from the membrane lung inspiratory gas sensor 125.

The second signal reception unit 152 is connected to the membrane lung expiratory gas sensor 126 and is configured to receive a membrane lung expiratory carbon dioxide ($CO_2$) concentration (oxygen content parameter) signal indicating the carbon dioxide concentration contained in membrane lung expiratory gas, which is sent from the membrane lung expiratory gas sensor 126.

The third signal reception unit 153 is connected to the ventilator inspiratory gas sensor 142 and is configured to receive an inspiratory carbon dioxide ($CO_2$) concentration (oxygen content parameter) signal indicating the carbon dioxide concentration contained in inspiratory gas to be delivered from the ventilator 140 to the native lung (NL), which is sent from the ventilator inspiratory gas sensor 142.

The fourth signal reception unit 154 is connected to the ventilator expiratory gas sensor 144 and is configured to receive an expiratory carbon dioxide ($CO_2$) concentration (oxygen content parameter) signal indicating the carbon dioxide concentration contained in expiratory gas discharged from the native lung (NL), which is sent from the ventilator expiratory gas sensor 144.

The fifth signal reception unit 155 is connected to the oxygen saturation sensor 117 and is configured to receive an oxygen saturation (blood-oxygenated state index) signal indicating the oxygen saturation degree of blood after being oxygenated by the membrane lung 120, which is sent from the oxygen saturation sensor 117.

The sixth signal reception unit 156 is connected to the pulse oximeter 148 and is configured to receive an oxygen saturation (blood-oxygenated state index) signal indicating the oxygen saturation degree of blood of the patient (living body, human body) P, which is sent from the pulse oximeter 148.

The first signal reception unit 151 to the sixth signal reception unit 156 output the received signals to the first calculation unit 160.

The first calculation unit 160 is configured of a computer and is connected to the first signal reception unit 151 to the sixth signal reception unit 156 as shown in FIG. 4 so that signals are input thereinto from these signal reception units. In the present embodiment (and the second embodiment described below), the computer means a configuration including at least a processor such as a CPU, and a memory capable of storing programs executable by the processor.

The first calculation unit 160 is configured such that gas flow rate signals (not shown) of the inspiratory gas and the expiratory gas are input thereinto from the membrane lung 120 and the ventilator 140 through cables (not shown).

In the present embodiment, gas supply amounts of the membrane lung 120 and the ventilator 140 are used as the gas flow rates of the inspiratory gas and the expiratory gas.

The first calculation unit 160 is connected to, for example, the first storage unit 165.

As shown in FIG. 4, the first calculation unit 160 includes, for example, a membrane lung carbon dioxide emission calculation unit 161, a ventilator carbon dioxide emission calculation unit 162, a membrane lung oxygen saturation (blood-oxygenated state index) calculation unit 163, and a living body oxygen saturation (blood-oxygenated state index) calculation unit 164.

The first calculation unit 160 refers to the first storage unit 165 as necessary and calculates various parameters based on signals input through the first signal reception unit 151 to the sixth signal reception unit 156. The first calculation unit 160 outputs the calculated results to the second calculation unit 170.

The first storage unit 165 is configured of, for example, a memory, a solid state drive (SSD), a hard disk drive or the like.

The first storage unit 165 stores constants, data tables, formulas for calculations, or the like, to which the membrane lung carbon dioxide emission calculation unit 161, the ventilator carbon dioxide emission calculation unit 162, the membrane lung oxygen saturation calculation unit 163, and the living body oxygen saturation calculation unit 164 refer at the time of calculating.

The second calculation unit 170 is configured of a computer and is connected to the first calculation unit 160 as shown in FIG. 4 so that the calculated results are input thereinto from the first calculation unit 160.

The second calculation unit 170 includes, for example, an assisted circulation ratio (assisted circulation contribution degree) calculation unit 171, and an oxygen saturation (blood-oxygenated state index) display unit 172.

As shown in FIG. 4, the membrane lung carbon dioxide emission calculation unit 161 receives a membrane lung inspiratory carbon dioxide ($CO_2$) concentration (oxygen content parameter) signal and a membrane lung expiratory carbon dioxide ($CO_2$) concentration (oxygen content parameter) signal through the first signal reception unit 151 and the second signal reception unit 152.

The membrane lung carbon dioxide emission calculation unit 161 receives a gas supply amount (i.e., gas flow rates of the inspiratory gas and the expiratory gas) signal (not shown) of the membrane lung 120.

The membrane lung carbon dioxide emission calculation unit 161 calculates the carbon dioxide ($CO_2$) emission amount (V'$CO_2$ (ML)) of the membrane lung 120 based on the received carbon dioxide ($CO_2$) concentration signals indicating the carbon dioxide concentrations contained in the inspiratory gas and the expiratory gas, and the received gas supply amount of the membrane lung 120.

Specifically, according to the following procedure shown in FIG. 5, the carbon dioxide ($CO_2$) concentration difference of the membrane lung 120 is calculated from the carbon dioxide ($CO_2$) concentration contained in the inspiratory gas of the membrane lung 120 and the carbon dioxide ($CO_2$) concentration contained in the expiratory gas thereof, the product of the carbon dioxide ($CO_2$) concentration difference occurring in the membrane lung 120 multiplied by the gas supply amount of the membrane lung 120 is calculated, and the carbon dioxide emission amount (V'$CO_2$ (ML)) of the membrane lung 120 is calculated.

(1) First, membrane lung inspiratory carbon dioxide concentration data is received through the first signal reception unit 151. (S101)

(2) Next, membrane lung expiratory carbon dioxide concentration data is received through the second signal reception unit 152. (S102)

(3) Next, the membrane lung carbon dioxide concentration difference is calculated based on the membrane lung inspiratory carbon dioxide concentration data and the membrane lung expiratory carbon dioxide concentration data. (S103)

The membrane lung carbon dioxide concentration difference is calculated by, for example, the following expression.

the membrane lung carbon dioxide concentration difference=the membrane lung expiratory carbon dioxide concentration–the membrane lung inspiratory carbon dioxide concentration (4) Membrane lung gas supply amount data is received from the membrane lung gas supply device 122. (S104)

(5) The membrane lung carbon dioxide emission amount is calculated. (S105)

The membrane lung carbon dioxide emission amount can be calculated by, for example, the following expression.

the membrane lung carbon dioxide emission amount ($V'CO_2(ML)$) = the carbon dioxide concentration difference in the membrane lung 120 × the gas supply amount of the membrane lung 120 =

(the membrane lung expiration carbon dioxide concentration – the membane lung inspiratory carbon dioxide concentration) × the gas supply amount of the membrane lung 120

At the time the above steps (S101) to (S105) are executed, the data tables (not shown) stored in the first storage unit 165 are referenced a % necessary.

The membrane lung carbon dioxide emission calculation unit 161 outputs the membrane lung inspiratory carbon dioxide ($CO_2$) concentration signal, the membrane lung expiratory carbon dioxide ($CO_2$) concentration signal, the membrane lung gas supply amount signal, and the calculated carbon dioxide emission amount (V'$CO_2$ (ML)) in the membrane lung to the assisted circulation ratio calculation unit 171.

As shown in FIG. 4, the ventilator carbon dioxide emission calculation unit 162 receives a ventilator inspiratory carbon dioxide ($CO_2$) concentration signal and a ventilator carbon dioxide ($CO_2$) concentration signal through the third signal reception unit 153 and the fourth signal reception unit 154.

The ventilator carbon dioxide emission calculation unit 162 receives a gas supply amount (i.e., gas flow rates of the inspiratory gas and the expiratory gas) signal (not shown) from the ventilator 140.

The ventilator carbon dioxide emission calculation unit 162 calculates the carbon dioxide ($CO_2$) emission amount (V'$CO_2$ (NL)) in the native lung (NL) based on the received carbon dioxide ($CO_2$) concentration signals indicating the carbon dioxide concentration contained in the inspiratory gas and the expiratory gas.

Specifically, according to the following procedure shown in FIG. 6, the carbon dioxide ($CO_2$) concentration difference in the ventilator 140 is calculated from the carbon dioxide ($CO_2$) concentration contained in the inspiratory gas of the ventilator 140 and the carbon dioxide ($CO_2$) concentration contained in the expiratory gas thereof, the product of the carbon dioxide ($CO_2$) concentration difference occurring in the ventilator 140 multiplied by the gas supply amount of the ventilator 140 is calculated, and the carbon dioxide emission amount (V'$CO_2$ (NL)) of the ventilator 140 is calculated. The carbon dioxide emission amount of the ventilator 140 is the carbon dioxide emission amount of the native lung (NL).

(1) First, ventilator inspiratory carbon dioxide concentration data is received through the third signal reception unit 153. (S201)

(2) Next, ventilator expiratory carbon dioxide concentration data is received through the fourth signal reception unit 154. (S202)

(3) Next, the ventilator carbon dioxide concentration difference (=the ventilator expiratory carbon dioxide concentration−the ventilator inspiratory carbon dioxide concentration) is calculated based on the ventilator inspiratory carbon dioxide concentration data and the ventilator expiratory carbon dioxide concentration data. (S203)

(4) The ventilator gas supply amount data is received from the ventilator 140. (S204)

(5) The ventilator carbon dioxide emission amount is calculated. (S205)

The ventilator carbon dioxide emission amount can be calculated by, for example, the following expression.

the ventilator carbon dioxide emission amount ($V'CO_2$(NL) = the carbon dioxide concentration difference in the ventilator 140 × the gas supply amount of the ventilator 140 =

(the ventilator expiratory carbon dioxide concentration − the ventilator inspiratory carbon dioxide concentration × the gas supply amount of the ventilator 140

At the time the above steps (S201) to (S205) am executed, the data tables (not shown) stored in the first storage unit 165 are referenced as necessary.

In the present embodiment, the carbon dioxide emission amount (V'$CO_2$ (NL)) of the native lung (NL) is calculated by the volume capno analysis or the like.

The ventilator carbon dioxide emission calculation unit 162 outputs the ventilator inspiratory carbon dioxide ($CO_2$) concentration signal, the ventilator expiratory carbon dioxide ($CO_2$) concentration signal, the ventilator gas supply amount signal, and the calculated carbon dioxide emission amount (V'$CO_2$ (NL)) in the native lung (NL) to the assisted circulation ratio calculation unit 171.

As shown in FIG. 4, the membrane lung oxygen saturation (blood-oxygenated state index) calculation unit 163 receives an oxygen saturation (blood-oxygenated state index) signal indicating the oxygen saturation degree of blood oxygenated in the membrane lung 120 front the oxygen saturation sensor 117 through the fifth signal reception unit 155.

The membrane lung oxygen saturation calculation unit 163 refers to, for example, the data tables (not shown) stored in the first storage unit 165 as necessary, calculates the membrane lung oxygen saturation degree (blood-oxygenated state index of the membrane lung) contained in the expiratory gas of the membrane lung 120, and outputs it to the oxygen saturation display unit 172.

As shown in FIG. 4, the living body oxygen saturation (blood-oxygenated state index) calculation unit 164 receives an oxygen saturation (blood-oxygenated state index) signal indicating the oxygen saturation degree of blood in the patient (living body) P from the pulse oximeter 148 through the sixth signal reception unit 156.

The living body oxygen saturation calculation unit 164 refers to, for example, the data tables (not shown) stored in the first storage unit 165 as necessary, calculates the oxygen saturation degree (blood-oxygenated state index) of the patient (living body) P. and outputs it to the oxygen saturation (blood-oxygenated state index) display unit 172.

The assisted circulation ratio (assisted circulation contribution degree) calculation unit 171 calculates the total emission amount of carbon dioxide ($CO_2$) of the whole living body, the assisted circulation ratio (ECMO Rate) (contribution degree of the assisted circulation) in the assisted circulation (V-V ECMO), and the respiratory efficiency by the weight of the patient (living body) P based on signals sent from the membrane lung carbon dioxide emission calculation unit 161 and the ventilator carbon dioxide emission calculation unit 162.

Figure 7:
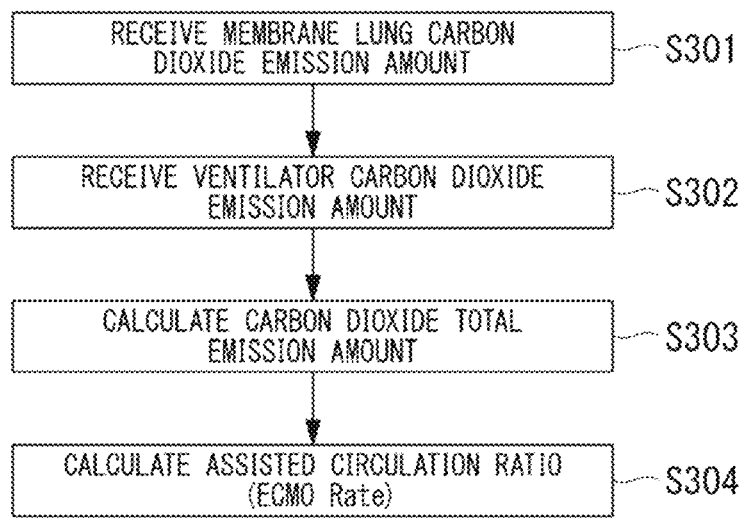
FIG. 7 is a flowchart showing an outline of a calculating procedure of an assisted circulation ratio of an assisted circulation ratio calculation unit for showing the schematic configuration of the monitoring apparatus pertaining to the first embodiment.

Specifically, the assisted circulation ratio calculation unit 171 calculates, according to the following procedure shown in FIG. 7, the carbon dioxide ($CO_2$) total emission amount of the whole living body from the membrane lung carbon dioxide ($CO_2$) emission amount and the ventilator carbon dioxide ($CO_2$) emission amount, and then calculates the assisted circulation ratio (ECMO Rate).

(1) First, the membrane lung carbon dioxide ($CO_2$) emission amount is obtained. (S301)

(2) Next, the ventilator carbon dioxide ($CO_2$) emission amount is obtained. (S302)

(3) Next, the carbon dioxide ($CO_2$) total emission amount is calculated based on the membrane lung carbon dioxide ($CO_2$) emission amount and the ventilator carbon dioxide ($CO_2$) emission amount. (S303)

The carbon dioxide ($CO_2$) total emission amount is calculated by, for example, the following expression.

the carbon dioxide total emission amount (V'$CO_2$)
=the membrane lung carbon dioxide emission amount (V'$CO_2$(ML))+the ventilator carbon dioxide emission amount (V'$CO_2$(NL))

(4) The assisted circulation ratio (ECMO Rate) (contribution degree of the assisted circulation) is calculated. (S304)

Figure 8:
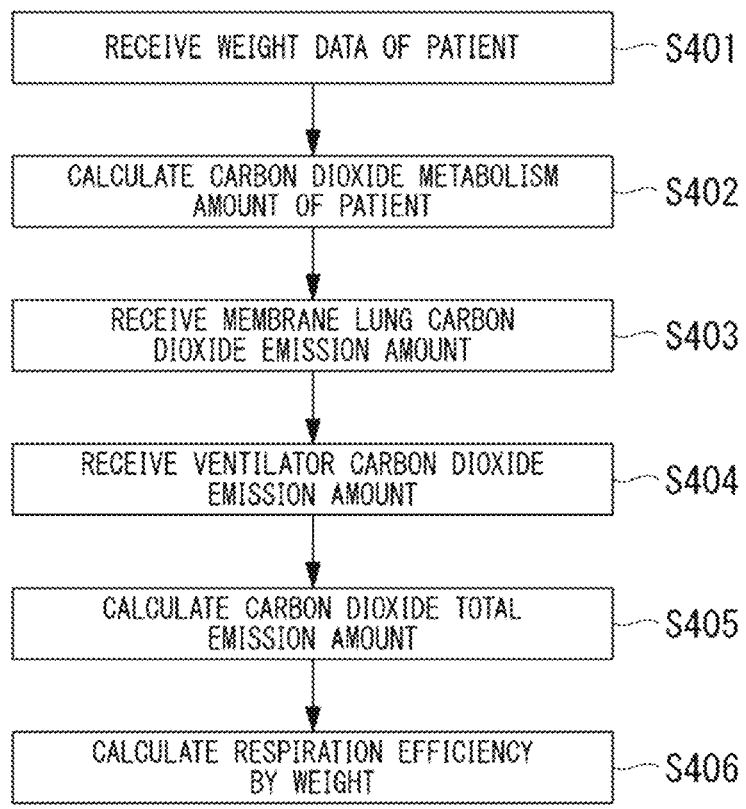
FIG. 8 is a flowchart showing an outline of a calculating procedure of respiratory efficiency by a weight in the assisted circulation ratio calculation unit for showing the schematic configuration of the monitoring apparatus pertaining to the first embodiment.
Figure 9:
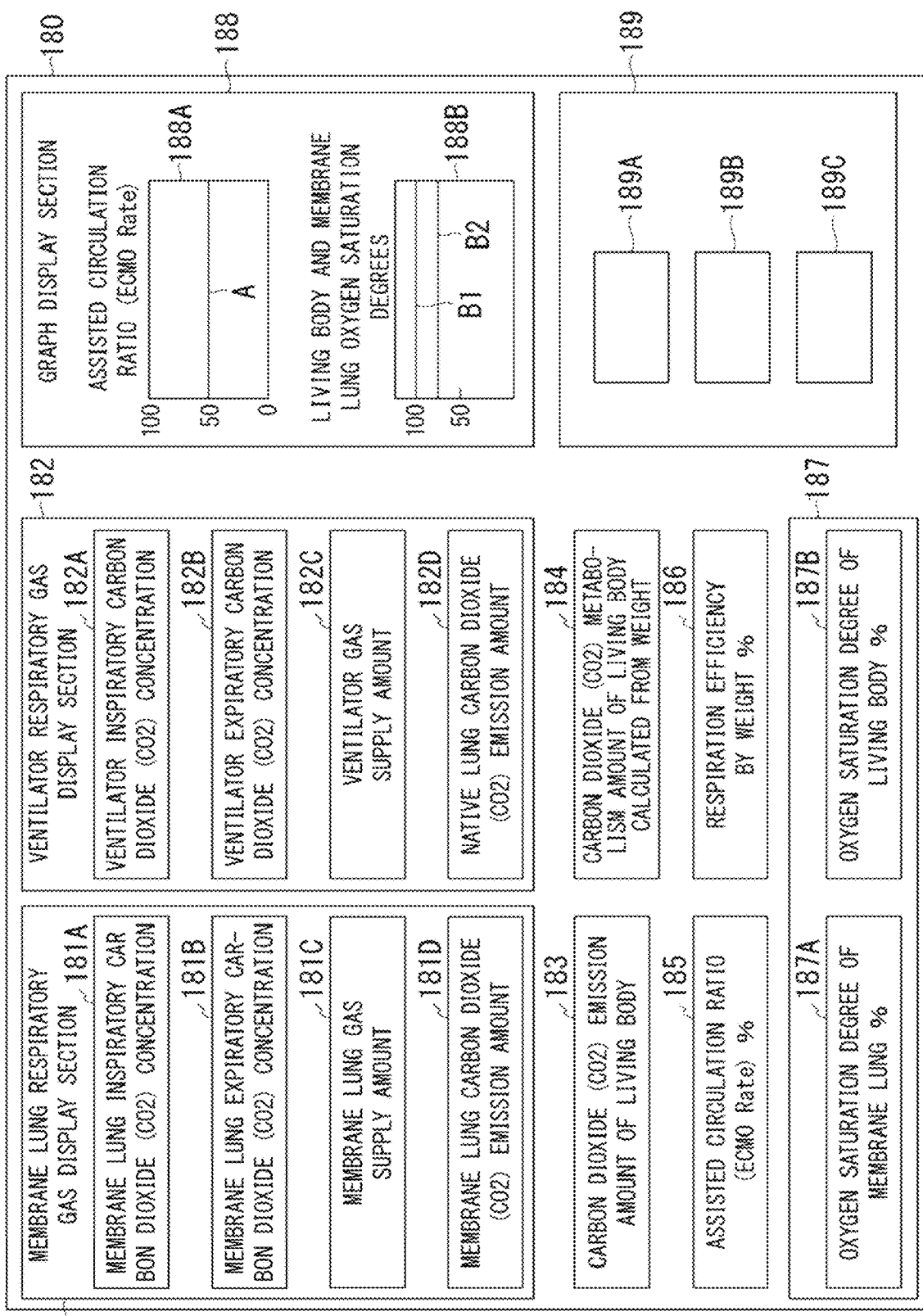
FIG. 9 is a conceptual diagram showing a schematic configuration of an LCD touch panel connecting to the monitoring apparatus pertaining to the first embodiment.

The assisted circulation ratio (ECMO Rate) is calculated by, for example, the following expression.

the assisted circulation ratio (ECMO Rate)=the membrane lung carbon dioxide emission amount (V'$CO_2$(ML))/the carbon dioxide total emission amount (V'$CO_2$) of the whole living body The assisted circulation ratio calculation unit 171 calculates, according to the following procedure shown in FIG. 8, the carbon dioxide ($CO_2$) total emission amount of the whole living body from the membrane lung carbon dioxide ($CO_2$) emission amount and the ventilator carbon dioxide ($CO_2$) emission amount, and calculates the respiratory efficiency by the weight of the patient P.

(1) First, weight data of the patient P is received. (S401)

The weight data of the patient P is entered using, for example, a numeric keypad (not shown) provided on the LCD touch panel 180.

(2) Next, the carbon dioxide metabolism (carbon dioxide ($CO_2$) amount by metabolism) estimated from the weight of the patient P is calculated. (S402)

Regarding the carbon dioxide ($CO_2$) amount of the patient P due to the assumed patient's (living body's) metabolism (at rest), an approximation thereof can be obtained by calculating using, for example, the following expression.

the carbon dioxide ($CO_2$ amount due to the assumed metabolism (at rest)=[1METS]×0.8×the weight of the patient P METs (MET: metabolic equivalent) denote an evaluation of exercise intensity, and 1 METs is denoted by the oxygen uptake amount at rest (3.5 ml/kg/min).

0.8: constant by respiratory quotient (3) Next, the membrane lung carbon dioxide ($CO_7$) emission amount is obtained. (S403)

(4) Next, the ventilator carbon dioxide ($CO_2$) emission amount is obtained. (S404)

(5) The respiratory efficiency by the weight of the patient P is calculated. (S406)

The respiratory efficiency by the weight of the native lung function of the patient P can be calculated by, for example, the following expression.

the respirator efficiency by the weight=the carbon dioxide total emission amount/the carbon dioxide ($CO_2$ amount due to the patient P's metabolism.

The assisted circulation ratio (assisted circulation contribution degree) calculation unit 171 outputs, for example, the membrane lung inspiratory carbon dioxide concentration, the membrane lung expiratory carbon dioxide concentration, the membrane lung gas supply amount, the membrane lung carbon dioxide emission amount, the ventilator inspiratory carbon dioxide concentration, the ventilator expiratory carbon dioxide concentration, the ventilator gas supply amount, the ventilator carbon dioxide emission amount, the assisted circulation ratio (ECMO Rate), and the respiratory efficiency by the weight of the native lung function of the patient P to the LCD touch panel (display) 180 continuously in real time.

The monitoring apparatus 100 may be configured to obtain parameters with regard to oxygen ($O_2$) instead of carbon dioxide ($CO_2$), and the assisted circulation ratio (assisted circulation contribution degree) calculation unit 171 may be configured to output, for example, the membrane lung inspiratory oxygen concentration, the membrane lung expiratory oxygen concentration, the membrane lung gas supply amount, the membrane lung oxygen uptake amount, the ventilator inspiratory oxygen concentration, the ventilator expiratory oxygen concentration, the ventilator gas supply amount, the native lung oxygen uptake amount, the assisted circulation ratio (ECMO Rate), and the respiratory efficiency by the weight of the native lung function of the patient P to the LCD touch panel (display) 180 continuously in real time.

The oxygen saturation display unit 172 receives the membrane lung oxygen saturation degree from the membrane lung oxygen saturation calculation unit 163 and receives the oxygen saturation degree of the patient (living body) P from the living body oxygen saturation calculation unit 164, for example.

The oxygen saturation display unit 172 outputs, for example, the membrane lung oxygen saturation degree and the oxygen saturation degree of the patient (living body) P to the LCD touch panel 180 and causes the LED touch panel 180 to display them.

The oxygen saturation display unit 172 may be configured to compare the membrane lung oxygen saturation degree and the oxygen saturation degree of the patient (living body) P with thresholds and to output alarms when abnormalities such as the degrees falling below the set thresholds are detected.

The thresholds are input using, for example, a numeric keypad (not shown) provided on the LCD touch panel 180 and are stored in a storage unit (not shown).

The oxygen saturation display unit 172 outputs signals relating to, for example, the membrane lung oxygen saturation degree, the living body oxygen saturation degree, and the alarms to the LCD touch panel (display) 180 in real time.

In the present embodiment, although the plurality of calculation units 160, 161, 162, 163, 164, 170, 171 and the display unit 172 are described, each or ones of these components may be configured of one computer, and the first calculation unit 160 and the second calculation unit 170 may be integrally configured of one computer.

As shown in FIG. 9, the LCD touch panel 180 includes, for example, a membrane lung respiration display section 181, a ventilator respiration display section 182, a carbon dioxide emission (living body-oxygenated state index) display section 183 indicating the carbon dioxide emission amount of the living body, a carbon dioxide metabolism display section 184 indicating the carbon dioxide metabolism of the living body calculated from the weight thereof, an assisted circulation ratio (ECMO Rate) display section 185, a respiratory efficiency display section 186 indicating the respiratory efficiency by the weight, an oxygen saturation (blood-oxygenated state index) display section 187, a graph display section 188, and a panel switch section (operation section) 189.

As shown in FIG. 9, the membrane lung respiration display section 181 includes, for example, a membrane lung inspiratory carbon dioxide ($CO_2$) concentration (membrane lung inspiratory gas concentration) display section 181A, a membrane lung expiratory carbon dioxide ($CO_2$) concentration (membrane lung expiratory gas concentration) display section 181B, a membrane lung gas supply (membrane lung inspiratory and expiratory gas flow rates) display section 181C, and a membrane lung carbon dioxide ($CO_2$) emission (gas exchange index) display section 181D.

In the present embodiment, the membrane lung inspiratory carbon dioxide ($CO_2$) concentration display section 181A, the membrane lung expiratory carbon dioxide ($CO_2$) concentration display section 181B, the membrane lung gas supply display section 181C, and the membrane lung carbon dioxide ($CO_2$) emission display section 181D display the membrane lung inspiratory carbon dioxide ($CO_2$) concentration, the membrane lung expiratory carbon dioxide ($CO_2$) concentration, the membrane lung gas supply amount, and the membrane lung carbon dioxide ($CO_2$) emission amount, which are output by the assisted circulation ratio calculation unit 171.

As shown in FIG. 9, the ventilator respiration display section 182 includes, for example, a ventilator inspiratory carbon dioxide ($CO_2$) concentration (ventilator inspiratory gas concentration) display section 182A, a ventilator expiratory carbon dioxide ($CO_2$) concentration (ventilator expiratory gas concentration) display section 182B, a ventilator gas supply (ventilator inspiratory and expiratory gas flow rates) display section 182C, and a native lung carbon dioxide emission (gas exchange index) display section 182D.

In the present embodiment, the ventilator inspiratory carbon dioxide ($CO_2$) concentration display section 182A, the ventilator expiratory carbon dioxide ($CO_2$) concentration display section 182B, the ventilator gas supply display section 182C, and the native lung carbon dioxide ($CO_2$) emission (gas exchange index) display section 182D display the ventilator inspiratory carbon dioxide ($CO_2$) concentration, the ventilator expiratory carbon dioxide ($CO_2$) concentration, the ventilator gas supply amount, and the carbon dioxide ($CO_2$) emission amount in native lung (NL), which are output by the assisted circulation ratio calculation unit 171.

The carbon dioxide metabolism display section 184 of the living body displays, for example, the carbon dioxide ($CO_2$) amount by the metabolism of the patient P output by the assisted circulation ratio calculation unit 171.

The assisted circulation ratio (ECMO Rate) display section 185 displays, for example, the assisted circulation ratio (ECMO Rate) output by the assisted circulation ratio calculation unit 171 numerically.

The respiratory efficiency display section 186 by the weight displays, for example, the respiratory efficiency by the weight of the patient P output by the assisted circulation ratio calculation unit 171 numerically.

The oxygen saturation display section 187 includes, for example, a membrane lung oxygen saturation display section 187A displaying the oxygen saturation degree of the membrane lung 120, and a living body oxygen saturation display section 187B displaying the oxygen saturation degree of the patient (living body) P.

The membrane lung oxygen saturation display section 187A and the living body oxygen saturation display section 187B receive oxygen saturation signals of the membrane lung 120 and the patient (living body) P output by the oxygen saturation display unit 172 and display them numerically.

As shown in FIG. 9, the graph display section 188 includes, for example, an assisted circulation ratio (ECMO Rate) display section 188A, and a living body and membrane lung oxygen saturation display section 188B.

The assisted circulation ratio (ECMO Rate) display section 188A displays, for example, a graph A of the assisted circulation ratio (ECMO Rate) output by the assisted circulation ratio calculation unit 171 in real time and chronologically.

The living body and membrane lung oxygen saturation display section 188B displays, for example, a graph B1 of the oxygen saturation degree of the membrane lung 120 output by the oxygen saturation display unit 172, and a graph B2 of the oxygen saturation degree of the patient (living body) P in real time and chronologically.

As shown in FIG. 9, the panel switch section (operation section) 189 includes, for example, a first touch portion 189A, a second touch portion 189B, and a third touch portion 189C.

The first touch portion 189A can determine which the oxygen ($O_2$), the carbon dioxide ($CO_2$), or both of the oxygen ($O_2$) and the carbon dioxide ($CO_2$) is used as the gas exchange index at the time the monitoring apparatus 100 monitors the assisted circulation (V-V ECMO) by, for example, operating a graphical user interface (GUI).

The second touch portion 189B can determine which the contribution degree of the assisted circulation (V-V ECMO) is displayed using, for example, the assisted circulation ratio (ECMO Rate) or a ratio of the membrane lung gas-exchanging amount to the ventilator gas-exchanging amount (the membrane lung gas-exchanging amount: the ventilator gas-exchanging amount) by touch operation.

The third touch portion 189C can selectively display, for example, the calculation results of Formulas (101) to (106).

According to the monitoring apparatus 100 pertaining to the first embodiment, the carbon dioxide emission amount in the assisted circulation system (V-V ECMO) 10 and the carbon dioxide emission amount by the ventilator 140 can be calculated.

According to the monitoring apparatus 100, in the assisted circulation system (V-V ECMO) 10, based on the membrane lung carbon dioxide emission amount, the native lung carbon dioxide emission amount, and the carbon dioxide total emission amount of the whole living body, the assisted circulation ratio (ECMO Rate) is calculated in real time and is displayed on the graph display section 188 of the LCD touch panel 180, so the contribution degree of the membrane lung 120 to the gas exchange of the patient P can be accurately grasped as a trend.

The dynamics of the assisted circulation (ECMO) and the status of the assisted circulation with respect to the overall respiration of the patient (living body) P can be accurately confirmed.

As a result, the gas-exchanging state of blood in the native lung (NL) and the membrane lung 120 can be accurately grasped.

According to the monitoring apparatus 100, the carbon dioxide emission amount in the membrane lung 120 is calculated based on the inspiratory gas and the expiratory gas of the membrane lung 120, so the carbon dioxide emission amount in the membrane lung 120 can be accurately calculated.

According to the monitoring apparatus 100, the carbon dioxide emission amount in the native lung (NL) is calculated based on the inspiratory gas and the expiratory gas of the ventilator 140, so the carbon dioxide emission amount in the native lung can be accurately and easily calculated.

As a result, the oxygenation status of blood by the native lung can be efficiently grasped.

According to the monitoring apparatus 100, the carbon dioxide emission amount in the native lung (NL) is calculated by the volume capno analysis, so the carbon dioxide emission amount in the native lung (NL) can be efficiently and accurately calculated.

According to the monitoring apparatus 100, the carbon dioxide ($CO_2$) amount due to the metabolism of the patient P calculated from the weight of the patient P is compared with the carbon dioxide total emission amount, so it is possible to efficiently grasp whether or not the gas exchange of blood of the patient P is appropriately performed.

According to the monitoring apparatus 100, the respiratory efficiency by the weight of the patient P is calculated based on the carbon dioxide ($CO_2$) metabolism amount calculated from the weight of the patient P, so it is possible to efficiently grasp whether or not the gas exchange of blood of the patient P is appropriately performed.

Second Embodiment

Hereinafter, an assisted circulation (V-A ECMO) pertaining to the second embodiment of the present invention is described with reference to FIGS. 10 and 11. In the description of the second embodiment, a component equivalent to that of the first embodiment may have the same reference sign attached thereto, and the description thereof may be omitted or simplified.

Figure 10:
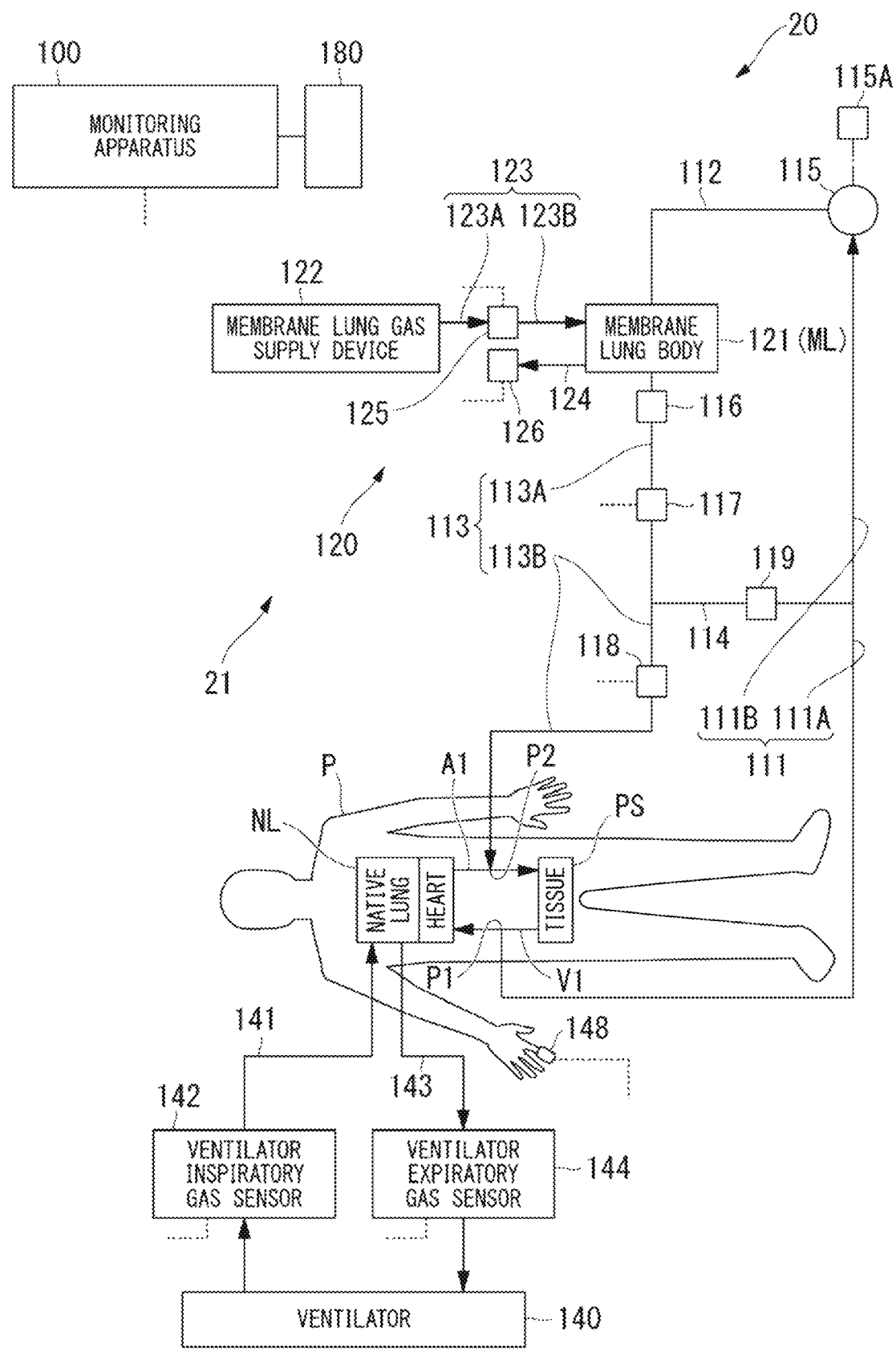
FIG. 10 is a conceptual diagram showing a schematic configuration of an assisted circulation (V-A ECMO) pertaining to a second embodiment of the present invention.

FIG. 10 is a conceptual diagram showing a schematic configuration of the assisted circulation (V-A ECMO) pertaining to the second embodiment of the present invention. The dotted lines shown in FIG. 10 simplify and denote electric cables connecting sensors and a monitoring apparatus 100.

Figure 11:
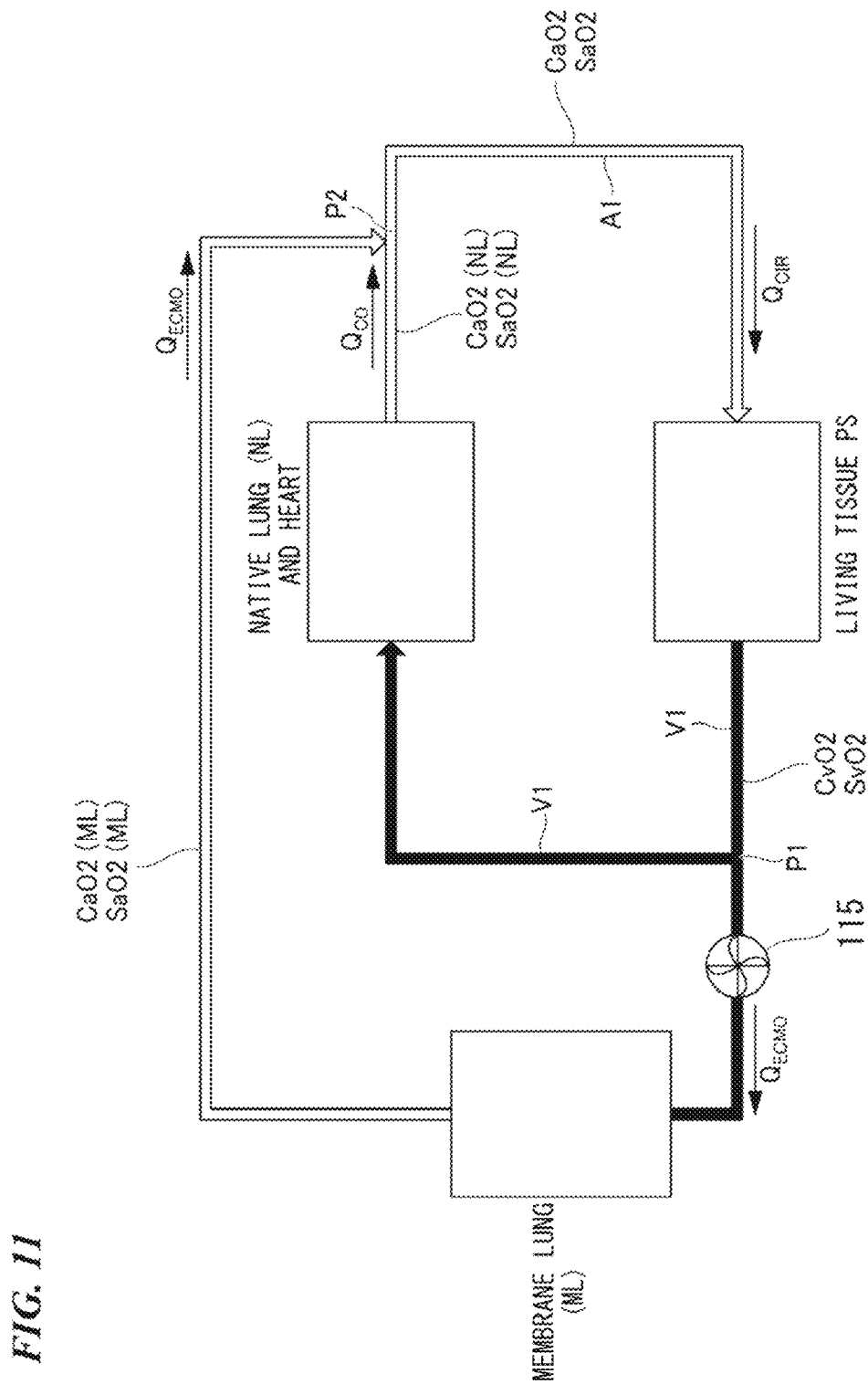
FIG. 11 is a conceptual diagram showing an overview of blood circulation of a patient having the assisted circulation (V-A ECMO) pertaining to the second embodiment applied thereto.

FIG. 11 is a conceptual diagram showing an overview of blood circulation of a patient having the assisted circulation (V-A ECMO) applied thereto.

In FIG. 10, a reference sign 20 represents an assisted circulation system (V-A ECMO).

The second embodiment is an example in which as shown in FIG. 10, a patient (living body) P is connected with, for example, the assisted circulation system (V-A ECMO) 20 and a ventilator 140.

In the second embodiment, the patient (living body) P is connected with, for example, the monitoring apparatus 100, the assisted circulation system (V-A ECMO) 20, an LCD touch panel 180, the ventilator 140, and a pulse oximeter (blood oxygenation index-measuring device) 148.

The assisted circulation system (V-A ECMO) 20 differs from the assisted circulation system (V-V ECMO) 10 in the following points. The others are equivalent to the first embodiment, so the same reference signs are attached thereto and the descriptions thereof are omitted.

That is, as shown in FIG. 10, the assisted circulation system (V-A ECMO) 20 differs therefrom in that blood removed from a vein V1 of the patient (living body, human body) P is circulated by a centrifugal pump (blood transfer pump) 115, and blood after gas exchange of blood is performed in a membrane lung 120 is returned to an artery A1 of the patient P.

Specifically, a second return line 113B is connected to the artery A1 and is configured such that blood sent out from the membrane lung 120 is transferred (returned) from a return point P2 to the artery A1 through the second return line 113B.

Although the configurations of the monitoring apparatus 100 and the LCD touch panel 180 can be arbitrarily set, in the second embodiment, the monitoring apparatus 100 and the LCD touch panel 180 have the same configurations as in the first embodiment.

The connections and operations of the monitoring apparatus 100 and the LCD touch panel 180 are the same as in the first embodiment, so the same reference signs are attached thereto and the descriptions thereof are omitted.

In the present embodiment, of the configuration of the assisted circulation system 20, a flow sensor 116, an oxygen saturation sensor 117, a blood transfer auto clamp 118, a recirculation clamp 119, and the membrane lung 120 configure an assisted circulation apparatus 21. In other words, the assisted circulation system 20 includes the assisted circulation apparatus 21, a blood removal line 111, a blood transfer line 112, a blood return line 113, a recirculation line 114, and the centrifugal pump 115, and the components 111, 112, 113, 114 and 115 can be handled as disposable products.

It is sufficient that the minimum configuration of the assisted circulation apparatus 21 includes the flow sensor 116, the oxygen saturation sensor 117, the blood transfer auto clamp 118, the recirculation clamp 119, and the membrane lung 120, and the assisted circulation apparatus 21 may be configured to include other components (for example, part of the above lines). The assisted circulation apparatus 21 may further include a drive unit 115A that drives the centrifugal pump 115. The assisted circulation apparatus 21 may further include the monitoring apparatus 100.

Next, the blood circulation when applying the assisted circulation system (V-A ECMO) is described with reference to FIG. 11.

In the patient (living body) P having the assisted circulation system (V-A ECMO) 20 applied thereto, as shown in FIG. 11, blood oxygenated in the native lung (NL) and having an oxygen content (oxygen content parameter) $CaO_2$ (NL), an oxygen saturation degree (blood-oxygenated state index) $SaO_2$ (NL), and a flow rate (cardiac output) $Q_{CO}$ is sent out by the heart to the artery A1.

On the other hand, in the assisted circulation (V-A ECMO), as shown in FIG. 1l, blood gas-exchanged and oxygenated by the membrane lung (ML) 120 and having an oxygen content (oxygen content parameter) $CaO_2$ (ML), an oxygen saturation degree (blood-oxygenated state index) $SaO_2$ (ML), and a flow rate (cardiac output) $Q_{CO}$ is sent out toward the artery A1 and joins blood sent out from the heart at the return point P2.

The blood joined at the return point P2 is mixed to become blood having an oxygen content $CaO_2$, an oxygen saturation degree $SaO_2$, and a flow rate $Q_{CIR}$ ($=Q_{CO}+Q_{ECMO}$) and flows through the artery A1 to living tissue PS.

In the blood flowed to the living tissue PS and having the oxygen content $CaO_2$, the oxygen saturation degree $SaO_2$, and the flow rate $Q_{CIR}$, oxygen thereof is consumed by metabolism in the living tissue PS, carbon dioxide is generated, and the oxygen content and the oxygen saturation degree thereof decrease to an oxygen content $CvO_2$ and an oxygen saturation degree $SvO_2$.

The blood having the flow rate (cm and decreased to the oxygen content $CvO_2$ and the oxygen saturation degree $SvO_2$ flows through the vein V1 toward the heart and the native lung (NL).

In the blood flowing through the vein V1 toward the heart and the native lung (NL) and having the oxygen content $CvO_2$, the oxygen saturation degree $SvO_2$, and the flow rate $Q_{CIR}$, blood with the flow rate $Q_{ECMO}$ is removed at a blood removal point P1 and flows to the membrane lung (ML) of the assisted circulation system (V-A ECMO) 20.

The blood removed and sent to the membrane lung (ML) is oxygenated by gas-exchanging the carbon dioxide ($CO_2$) with the oxygen ($O_2$) in the membrane lung (ML) and returns to the artery A1 at the return point P2.

On the other hand, the blood with the flow rate $Q_{CO}$ ($=Q_{CIR}-Q_{ECMO}$) that has not removed at the blood removal point P1 flows directly toward the heart through the vein V1.

The blood is oxygenated in the native lung (Nl), becomes blood having the oxygen content $CaO_2$ (NL), the oxygen saturation degree $SaO_2$ (NL), and the flow rate (cardiac output) $Q_{CO}$, and is sent out to the artery A1.

In the blood circulation shown in FIG. 11, blood is oxygenated by [$DaO_2-DvO_2$] shown in above Formula (101) in the membrane lung (ML) and the native lung (NL).

The blood circulation in the assisted circulation (V-A ECMO) can be described by focusing on either the assisted circulation flow rate $Q_{ECMO}$ or the arterial blood oxygen content $CaO_2$.

[Case of Focusing on Assisted Circulation Flow Rate $Q_{ECMO}$]

When focusing on the assisted circulation flow rate $Q_{ECMO}$, in the blood circulation in the assisted circulation (V-A ECMO). Formula (101) to Formula (106) hold, which are described in the assisted circulation (V-V ECMO) pertaining to the first embodiment. The content thereof is the same as the first embodiment, so the description thereof is omitted.

[Case of Focusing on Arterial Blood Oxygen Content $CaO_2$]

When assuming that blood flowing through the artery A1 to the living tissue PS has an arterial blood oxygen content $CaO_2$ and a circulating blood flow rate $Q_{CIR}$, an arterial blood oxygen transfer rate $DaO_2$ can be expressed by following Formula (201).

[Expression 7]
$$D_aO_2 = C_aO_2 \times Q_{CIR} \quad (201)$$

When applying the assisted circulation (V-A ECMO), the circulating blood flow rate $Q_{CIR}$ is equal to the sum of the assisted circulation flow rate $Q_{ECMO}$ and the cardiac output $Q_{CO}$, so the circulating blood flow rate $Q_{CIR}$ can be expressed by following Formula (202).

[Expression 8]
$$Q_{CIR} = Q_{ECMO} + Q_{CO} \quad (202)$$

On the other hand, since the mass of the oxygen is conserved, the arterial blood oxygen content $CaO_2$ can be expressed as following Formula (203) by using the oxygen content $CaO_2$ (NL) after gas exchange in the native lung (NL), the circulating blood flow rate Q a, the oxygen content $CaO_2$ (ML) after gas exchange in the membrane long (ML), and the flow rate $Q_{ECMO}$ of blood oxygenated in the membrane lung (ML).

[Expression 9]
$$C_aO_2 = \frac{C_aO_2(NL) \times Q_{CO} + C_aO_2(ML) \times Q_{ECMO}}{Q_{CIR}} \quad (203)$$

Since the carbon dioxide total emission amount V'CO$_2$ of the whole living body is equal to the sum of the carbon dioxide emission amount V'CO$_2$ (ML) of the membrane lung (ML) and the carbon dioxide emission amount V'CO$_2$ (NL) of the native lung (NL). Formula (203) is substituted for Formula (201), the left side of the resulting formula is divided by the carbon dioxide total emission amount V'CO$_2$ of the whole living body, the right side thereof is divided by the sum of the carbon dioxide emission amount V'CO$_2$ (NL) of the native lung (NL) and the carbon dioxide emission amount V'CO$_2$ (ML) of the membrane lung (ML), and the result is expressed by following Formula (204).

[Expression 10]
$$\frac{D_aO_2}{V'CO_2} = \frac{C_aO_2(NL) \times Q_{CO} + C_aO_2(ML) \times Q_{EMCO}}{V'CO_2(NL) + V'CO_2(ML)} \quad (204)$$

Since it is difficult to directly measure the cardiac output $Q_{CO}$ in above Formulas (202) to (204), a general estimate of the carbon dioxide emission amount V'CO$_2$ (ML) in the membrane lung (ML) is appropriately used.

The calculation results of above Formulas (203) to (204) may be selectively displayed by operating the third touch portion 189C, for example.

The present invention is not limited to the above embodiments, and various modifications can be adopted within the scope of the present invention.

For example, in the above embodiments, the case of applying the monitoring apparatus 100 to the monitoring of the assisted circulation system (V-V ECMO) 10 and the assisted circulation system (V-A ECMO) 20 is described, but the monitoring apparatus 100 may be applied to, for example, the monitoring of an assisted circulation (V-V-A ECMO).

In the above embodiments, the case of using the ventilator 140 together with the assisted circulation system 10 or 20 is described, but it is possible to arbitrarily determine whether or not the ventilator 140 is used, and the carbon dioxide emission amount and the oxygen uptake amount may be calculated by the inspiratory gas and the expiratory gas when breathing using an oxygen mask or the like instead of the ventilator 140.

In the above embodiments, the case is described where the gas sensor used for obtaining the gas exchange index at the time of calculating the contribution degree of the membrane lung 120 in the assisted circulation system (circuit) 10 is the carbon dioxide concentration sensor connected to the membrane lung 120 and the ventilator 140, but for example, an oxygen concentration sensor connected to the membrane lung 120 and the ventilator 140 may be applied thereto, and the assisted circulation ratio may be calculated. The assisted circulation ratio may be calculated using both of the carbon dioxide concentration sensor and the oxygen concentration sensor.

The configurations and arrangement positions of the membrane lung inspiratory gas sensor 125, the membrane lung expiratory gas sensor 126, the ventilator inspiratory gas sensor 142, and the ventilator expiratory gas sensor 144 can be arbitrarily set.

For example, the membrane lung inspiratory line 123 and the membrane lung expiratory line 124 may be provided with a sampling circuit (not shown), and one gas sensor may be used both as the ventilator inspiratory gas sensor 142 and the ventilator expiratory gas sensor 144.

In the above embodiments, the case is described where the gas exchange index corresponding to the oxygen uptake amount is calculated by the gas-exchanged carbon dioxide concentration obtained by the membrane lung inspiratory gas sensor 125, the membrane lung expiratory gas sensor 126, the ventilator inspiratory gas sensor 142, and the ventilator expiratory gas sensor 144, but a configuration may be adopted where the gas exchange index is calculated by, for example, measuring the content of other gas (for example, anesthesia gas or the like) contained in respiratory gas, which can determine the content of carbon dioxide or oxygen.

In the above embodiments, the case where the monitoring apparatus 100 calculates the carbon dioxide emission amount in the native lung (NL) by the volume capno analysis is described, but a configuration may be adopted where the carbon dioxide emission amount in native lung (NL) calculated by the volume capno analysis is input from the outside.

For example, in the above embodiments, the case where the blood transfer pump is the centrifugal pump 115 is described, but instead of the centrifugal pump 115, for example, a roller pump may be used in which a rotating roller rotates and squeezes a flexible tube to aspirate and deliver blood.

In the above embodiments, the various calculations in the monitoring apparatus 100 are described using mathematical formulas, but the above mathematical formulas are an example, it is not limited to the above mathematical formulas, and other formulas and calculation methods may be used.

In the above embodiments, an example of a schematic configuration of a flowchart for showing the operation of the monitoring apparatus 100 is described, but a method (algorithm) other than the above flowchart may be used for control.

In the above embodiments, the case of applying the monitoring apparatus 100 to the monitoring of the assisted circulation of the patient (human body, living body) P is described, but it may be applied to the assisted circulation of animals (living body) or the like.

Either one or both of the first calculation unit 160 and the second calculation unit 170 described in the first and second embodiments above may correspond to the "calculation unit" in the present invention.

On the other hand, as described above, the monitoring apparatus 100 of the first and second embodiments includes the first signal reception unit 151 to the sixth signal reception unit 156, the first calculation unit 160, the second calculation unit 170, and the first storage unit 165, but it is not limited thereto, and the monitoring apparatus 100 may include at least the assisted circulation ratio calculation unit 171. In this case, the assisted circulation ratio calculation unit 171 corresponds to the "calculation unit" in the present invention.

INDUSTRIAL APPLICABILITY

According to a monitoring apparatus pertaining to the present invention, the gas-exchanging state of blood in the native lung and the membrane lung of a patient connected with an assisted circulation apparatus can be accurately grasped, so it is industrially applicable.

The invention claimed is:

1. A monitoring apparatus for being applied to an assisted circulation apparatus, the assisted circulation apparatus being connected to a living body, transferring blood removed from the living body to a membrane lung by a blood transfer pump, and gas-exchanging and oxygenating the blood in the membrane lung in parallel with a native lung, the monitoring apparatus for monitoring an oxygenation state of blood in the living body, the monitoring apparatus comprising:

a display;

at least a memory configured to store programs; and at least a processor configured to execute the programs to:

calculate a ratio of a first blood-oxygenated state index to a sum of the first blood-oxygenated state index and a second blood-oxygenated state index, wherein the first blood-oxygenated state index indicates an oxygenation state of blood by the membrane lung, the second blood-oxygenated state index indicates an oxygenation state of blood by the native lung, and the ratio expresses a contribution degree of the assisted circulation apparatus to the living body, calculate the first blood-oxygenated state index based on a gas-exchanging amount of blood in the membrane lung, calculate the gas-exchanging amount of blood in the membrane lung based on at least one of a carbon dioxide emission amount in the membrane lung and an oxygen uptake amount in the membrane lung, calculate the at least one of the carbon dioxide emission amount in the membrane lung and the oxygen uptake amount in the membrane lung using measurement results of a first sensor configured to measure inspiratory gas and expiratory gas of the membrane lung, calculate the second blood-oxygenated state index based on a gas-exchanging amount of blood in the native lung, calculate the gas-exchanging amount of blood in the native lung based on at least one of a carbon dioxide emission amount in the native lung and an oxygen uptake amount in the living body, calculate the at least one of the carbon dioxide emission amount in the native lung and the oxygen uptake amount in the living body using measurement results of a second sensor configured to measure inspiratory gas and expiratory gas of the native lung, compare the sum of the first blood-oxygenated state index and the second blood-oxygenated state index with a blood-oxygenated state index indicating an oxygenation state of blood based on metabolism estimated from a weight of the living body, and output continuously in real time a result of the comparison to the display for an operator to institute a change in treatment of the living body.

2. The monitoring apparatus according to claim 1, wherein the processor executes the programs to calculate the carbon dioxide emission amount in the native lung by volume capno analysis.

3. The monitoring apparatus according to claim 1, wherein the processor executes the programs to calculate at set time intervals.

4. An assisted circulation apparatus comprising the monitoring apparatus according to claim 1.

5. The monitoring apparatus according to claim 1, wherein the processor is further configured to execute the programs to:

display a trend graph on the display to show changes in the calculated ratio over time to enable the operator to visualize native lung recovery progress.

6. The monitoring apparatus according to claim 1, wherein the processor is further configured to execute the programs to:

compare the first blood-oxygenated state index with a predetermined threshold value, and display an alert on the display when the first blood-oxygenated state index is less than the predetermined threshold value.

* * * * *